(12) United States Patent
Youfu et al.

(10) Patent No.: US 7,722,784 B2
(45) Date of Patent: May 25, 2010

(54) LIQUID CRYSTAL COMPOSITION, LIQUID CRYSTAL DEVICE, REFLECTION DISPLAY MATERIAL, LIGHT MODULATING MATERIAL, AND ANTHRAQUINONE COMPOUND

(75) Inventors: Katsuyuki Youfu, Kanagawa (JP); Koji Takaku, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/203,517

(22) Filed: Sep. 3, 2008

(65) Prior Publication Data

US 2009/0074991 A1 Mar. 19, 2009

(30) Foreign Application Priority Data

Sep. 18, 2007 (JP) ............................. 2007-241472

(51) Int. Cl.
*C09K 19/00* (2006.01)
*C09K 19/06* (2006.01)
*C09K 19/52* (2006.01)

(52) U.S. Cl. ........................... 252/299.62; 252/299.01; 252/299.6; 428/1.1; 428/1.4; 430/20; 349/56; 564/427; 568/43; 568/326

(58) Field of Classification Search ............ 252/299.01, 252/299.6, 299.62; 428/1.1, 1.4; 430/20; 349/56; 564/427; 568/43, 326

See application file for complete search history.

(56) References Cited

U.S. PATENT DOCUMENTS

| 5,026,505 | A | | 6/1991 | Kaneko et al. | |
| 6,033,598 | A | * | 3/2000 | Kaneko et al. | ............ 252/299.1 |
| 6,033,742 | A | * | 3/2000 | Iwanaga et al. | ............ 428/1.31 |
| 6,057,906 | A | * | 5/2000 | Iwanaga et al. | ............. 349/182 |
| 6,656,542 | B2 | * | 12/2003 | Iwanaga et al. | .............. 428/1.1 |

FOREIGN PATENT DOCUMENTS

| JP | 58-57488 A | 4/1983 |
| JP | 62-277471 A | 12/1987 |
| JP | 1-252691 A | 10/1989 |

OTHER PUBLICATIONS

"Handbook of Liquid Crystals", written by B. Bahadur, edited by D. Demus, J. Goodby, G. W. Gray, H. W. Spiess, and V. Vill, vol. 2A, published by Wiley-VCH, 1998, Chapters 3 and 4, pp. 257-302.

* cited by examiner

*Primary Examiner*—Geraldina Visconti
(74) *Attorney, Agent, or Firm*—Birch, Stewart, Kolasch & Birch, LLP.

(57) ABSTRACT

The liquid crystal composition of the present invention contains a compound represented by the following Formula (1) and a liquid crystal. In Formula (1), at least one among $R^1$ to $R^7$ is a liquid crystalline substituent, and those among $R^1$ to $R^7$ that are not a liquid crystalline substituent each independently represent a hydrogen atom or a substituent. X and Y each independently represent an alkyl group, a halogen atom, an alkoxy group, or an alkylthio group. Z represents an alkyl group having 3 or more carbon atoms, an acyl group, or an aryl group. A represents an oxygen atom, a sulfur atom, or a nitrogen atom. n represents 0 or 1. The liquid crystal device, reflection display material, and light modulating material of the invention contain the liquid crystal composition.

Formula (1)

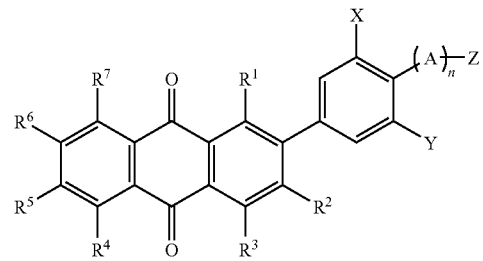

15 Claims, No Drawings

LIQUID CRYSTAL COMPOSITION, LIQUID CRYSTAL DEVICE, REFLECTION DISPLAY MATERIAL, LIGHT MODULATING MATERIAL, AND ANTHRAQUINONE COMPOUND

CROSS REFERENCE TO RELATED APPLICATIONS

This application claims priority under 35 USC 119 from Japanese Patent Application No. 2007-241472, the disclosure of which is incorporated herein by reference.

BACKGROUND OF THE INVENTION

1. Field of the Invention

The present invention relates to liquid crystal compositions, liquid crystal devices, reflection display materials, light modulating materials, and anthraquinone compounds.

2. Description of the Related Art

Many types of liquid crystal devices (liquid crystal display devices) have been proposed. Because guest-host type liquid crystal devices use no polarizer, those of reflection type are expected to be bright image displays and those of transmission type are expected to be light modulating materials which are bright when they are transparent. In guest-host type liquid crystal devices, a dichroic dye is dissolved in a liquid crystal, and coloring and decoloring are switched by change in alignment of the dichroic dye synchronized with the movement of the liquid crystal due to an electric field.

The guest-host type device is described for example in "Handbook of Liquid Crystals", written by B. Bahadur, edited by D. Demus, J. Goodby, G. W. Gray, H. W. Spiess, and V. Vill, Vol. 2A, published by Wiley-VCH, 1998, Chapters 3 and 4, pages 257-302. Dichroic dyes used in guest-host type liquid crystal devices are required to exhibit proper absorption properties, a high order parameter, a high solubility in host liquid crystal, durability, or the like.

From the viewpoint of dichroic ratio, solubility and durability, especially azo- and anthraquinone dichroic dyes have been investigated widely. However, azo dichroic dyes are defective in light resistance though they are good with respect to order parameter and solubility.

On the other hand, anthraquinone dyes have low solubility in host liquid crystals though they have high light resistance. In order to reconcile the solubility and the order parameter, many researchers have made various studies, e.g., introduction of a liquid crystalline substituent into an anthraquinone skeleton and increase in compatibility with liquid crystal. For example, Japanese Patent Application Laid-Open (JP-A) Nos. 58-57488, 1-252691, and 62-277471 can be referred to. However, the solubility is still unsatisfactory.

SUMMARY OF THE INVENTION

A first aspect of the present invention is a liquid crystal composition comprising a compound represented by the following Formula (1) and liquid crystal.

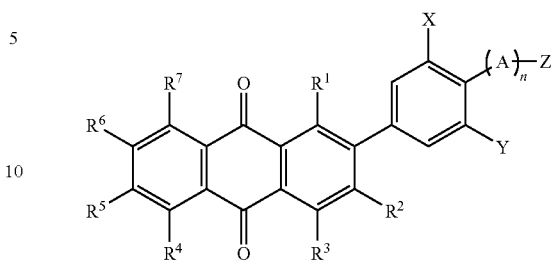

Formula (1)

In Formula (1), at least one among $R^1, R^2, R^3, R^4, R^5, R^6$ or $R^7$ is a liquid crystalline substituent, and those among $R^1, R^2, R^3, R^4, R^5, R^6$ and $R^7$ that are not a liquid crystalline substituent each independently represent a hydrogen atom or a substituent. X and Y each independently represent an alkyl group, a halogen atom, an alkoxy group, or an alkylthio group. Z represents an alkyl group having 3 or more carbon atoms, an acyl group, or an aryl group. A represents an oxygen atom, a sulfur atom, or a nitrogen atom. n represents 0 or 1.

A second aspect of the present invention is a liquid crystal device comprising a pair of electrodes at least one of which is a transparent electrode, and a liquid crystal layer disposed between the pair of electrodes which comprises the liquid crystal composition according to the first aspect.

A third aspect of the present invention is a reflection display material comprising the liquid crystal device according to the second aspect.

The fourth aspect of the present invention is a light modulating material comprising the liquid crystal device according to the second aspect.

A fifth aspect of the present invention is a compound represented by the following Formula (1).

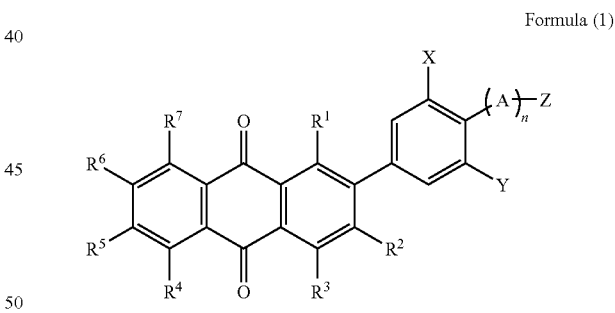

Formula (1)

In Formula (1), at least one among $R^1, R^2, R^3, R^4, R^5, R^6$ or d $R^7$ is a liquid crystalline substituent, and those among $R^1, R^2, R^3, R^4, R^5, R^6$ or $R^7$ that are not a liquid crystalline substituent each independently represent a hydrogen atom or a substituent. X and Y each independently represent an alkyl group, a halogen atom, an alkoxy group, or an alkylthio group. Z represents an alkyl group having three or more carbon atoms, an acyl group, or an aryl group. A represents an oxygen atom, a sulfur atom, or a nitrogen atom. n represents 0 or 1.

DETAILED DESCRIPTION OF THE INVENTION

<Liquid Crystal Composition>

The liquid crystal composition of the present invention includes a compound represented by the following Formula (1), which may hereinafter be referred to as a "compound according to the present invention" or a "dichroic dye of the present invention", and liquid crystal.

As in the compound of the following Formula (1), by linking a phenyl group having substituents at its 3-, 4- and 5-positions directly to the 2-position of a dichroic dye having an anthraquinone skeleton, the position slightly apart from the anthraquinone body becomes sterically bulky. It was found that, by further introducing a liquid crystalline group to the anthraquinone skeleton, not only does the order parameter increases dramatically, but also the solubility in liquid crystal increases. Moreover, an unexpected effect is obtained in that, even if this dichroic dye is dissolved in liquid crystal in a high concentration, an increase in viscosity is suppressed.

The present invention will be described in detail below. In the present specification " . . . to . . . " represents a range including the numeral values represented before and after "to" as a minimum value and a maximum value, respectively.

(Dichroic Dye)

The dichroic dye of the present invention is a compound of the following Formula (1) that has a phenyl group having substituents at its 3-, 4- and 5-positions, which may hereinafter be referred to as a "specific phenyl group", at the 2-position of the dichroic dye having an anthraquinone skeleton, and that has at least one liquid crystalline substituent in the molecule.

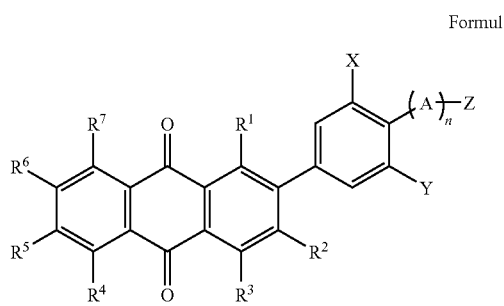

Formula (1)

In Formula (1), at least one among $R^1$, $R^2$, $R^3$, $R^4$, $R^5$, $R^6$ or $R^7$ is a liquid crystalline substituent, and those among $R^1$, $R^2$, $R^3$, $R^4$, $R^5$, $R^6$ and $R^7$ that are not a liquid crystalline substituent each independently represent a hydrogen atom or a substituent. X and Y each independently represent an alkyl group, a halogen atom, an alkoxy group, or an alkylthio group. Z represents an alkyl group having 3 or more carbon atoms, an acyl group, or an aryl group. A represents an oxygen atom, a sulfur atom, or a nitrogen atom. n represents 0 or 1.

It is assumed that when the dichroic dye having an anthraquinone skeleton has a specific phenyl group at the 2-position and a liquid crystalline substituent exists in the molecule in Formula (1), an increased order parameter is obtained because the anthraquinone skeleton has a long apparent molecular major axis and therefore it is highly rod-like and, as a result, the fluctuation in the liquid crystal is reduced. It is also assumed that when a sterically bulky substituent is introduced to a proper position, aggregation among colorant molecules is inhibited and, as a result, the solubility increases without a decrease in the order parameter. However, the present invention is not limited by such an assumption. Further, a high level of light resistance, which is an advantage of dichroic dyes having an anthraquinone skeleton, is also maintained.

The compound represented by Formula (1) preferably has a structure having no symmetry axis. It is expected that, due to the absence of a symmetry axis, the crystallization speed of the dye will become extremely low, and it is also expected that this will lead to an increase in solubility.

The substituents among $R^1$ to $R^7$ that are not a liquid crystalline substituent in Formula (1) may each independently be a substituent selected from the following substituent group R.

—Substituent Group R—

Halogen atoms, alkyl groups (including a cycloalkyl group), alkenyl groups (including a cycloalkenyl group), alkynyl groups, aryl groups, heterocyclic groups, a cyano group, a hydroxyl group, a nitro group, a carboxyl group, alkoxy groups, aryloxy groups, heterocyclic oxy groups, acyloxy groups, carbamoyloxy groups, amino groups (including an anilino group), acylamino groups, aminocarbonylamino groups, alkoxycarbonylamino groups, aryloxycarbonylamino groups, alkyl or aryl sulfonylamino groups, a mercapto group, alkylthio groups, arylthio groups, heterocyclic thio groups, a sulfamoyl group, a sulfo group, alkyl or aryl sulfinyl groups, alkyl or aryl sulfonyl groups, acyl groups, aryloxycarbonyl groups, alkoxycarbonyl groups, a carbamoyl group, aryl or heterocyclic azo groups, an imido group, a phosphino group, a phosphinyl group, a phosphinyloxy group, a phosphinylamino group, or a silyl group are included.

More particularly, examples of the halogen atom include a chlorine atom, a bromine atom or an iodine atom.

The alkyl groups are preferably alkyl groups having 1 to 30 carbon atoms, examples of which include methyl, ethyl, n-propyl, isopropyl, tert-butyl, n-octyl, eicosyl, 2-chloroethyl, 2-cyanoethyl or 2-ethylhexyl. The alkyl groups may be straight-chain, branched or cyclic, and these may be either substituted or unsubstituted. The cycloalkyl groups are preferably substituted or unsubstituted cycloalkyl groups having 3 to 30 carbon atoms, examples of which include cyclohexyl, cyclopentyl, 4-n-dodecyleyclohexyl, bicyclo[1,2,2]heptan-2-yl, or bicyclo[2,2,2]octan-3-yl. Tricyclo structure or the like, which have more ring structures, are also included. The alkyl groups in the substituents explained hereafter (for example, an alkyl group included in an alkylthio group) also represent alkyl groups of this concept.

The alkenyl groups are preferably alkenyl groups having 2 to 30 carbon atoms, examples of which include vinyl, allyl, prenyl, geranyl or oleyl. The alkenyl groups may be straight-chain, branched or cyclic, and these may be either substituted or unsubstituted. The cycloalkenyl groups are preferably substituted or unsubstituted cycloalkenyl groups having 3 to 30 carbon atoms (that is, monovalent groups each resulting from removal of one hydrogen atom from a cycloalkene having 3 to 30 carbon atoms), examples of which include 2-cyclopenten-1-yl, 2-cyclohexen-1-yl, bicyclo[2,2,1]hept-2-en-1-yl, or bicyclo[2,2,2]oct-2-en-4-yl. These may be either substituted or unsubstituted.

The alkynyl groups are preferably alkynyl groups having 2 to 30 carbon atoms, examples of which include ethynyl, propargyl or trimethylsilylethynyl. These may be either substituted or unsubstituted.

The aryl groups are preferably aryl groups having 6 to 30 carbon atoms, examples of which include phenyl, p-tolyl, naphthyl, p-nitrophenyl, p-cyanophenyl, p-fluorophenyl, m-chlorophenyl or o-hexadecanoylaminophenyl. These may be either substituted or unsubstituted.

The heterocyclic groups are preferably monovalent groups each resulting from removal of one hydrogen atom from a 5- or 6-membered heterocyclic compound, which may be either aromatic or non-aromatic. More preferred are heterocyclic groups having 3 to 30 carbon atoms, example of which include 2-furil, 2-thienyl, 2-pyrimidinyl, 2-benzothiazolyl, quinolyl, thiazolyl, benzoxazolyl or benzoimidazolyl. These may be either substituted or unsubstituted.

The alkoxy groups are preferably alkoxy groups having 1 to 30 carbon atoms, examples of which include methoxy, ethoxy, isopropoxy, tert-butoxy, n-octyloxy, or 2-methoxyethoxy. These may be either substituted or unsubstituted.

The aryloxy groups are preferably aryloxy groups having 6 to 30 carbon atoms, examples of which include phenoxy, 2-methylphenoxy, 4-tert-butylphenoxy, 3-nitrophenoxy, or 2-tetradecanoylaminophenoxy. These may be either substituted or unsubstituted.

The heterocyclic oxy group are preferably heterocyclic oxy group having 2 to 30 carbon atoms, examples of which include 1-phenyltetrazol-5-oxy, or 2-tetrahydropyranyloxy. These may be either substituted or unsubstituted.

The acyloxy groups are preferably a formyloxy group, alkylcarbonyloxy groups having 2 to 30 carbon atoms, or arylcarbonyloxy groups having 6 to 30 carbon atoms, examples of which include formyloxy, acetyloxy, pivaloyloxy, stearoyloxy, benzoyloxy, or p-methoxyphenylcarbonyloxy. These may be either substituted or unsubstituted.

The carbamoyloxy groups are preferably carbamoyloxy groups having 1 to 30 carbon atoms, examples of which include N,N-dimethylcarbamoyloxy, N,N-diethylcarbamoyloxy, morpholinocarbonyloxy, N,N-di-n-octylaminocarbonyloxy, or N-n-octylcarbamoyloxy. These may be either substituted or unsubstituted.

The amino groups are preferably an amino group, alkylamino groups having 1 to 30 carbon atoms or anilino groups having 6 to 30 carbon atoms, examples of which include amino, methylamino, dimethylamino, anilino, N-methylanilino, or diphenylamino. These may be either substituted or unsubstituted.

The acylamino groups are preferably a formylamino group, alkylcarbonylamino groups having 1 to 30 carbon atoms or arylcarbonylamino groups having 6 to 30 carbon atoms, examples of which include formylamino, acetylamino, pivaloylamino, lauroylamino, benzoylamino, 3,4,5-tri-n-octyloxyphenylcarbonylamino. These may be either substituted or unsubstituted.

The aminocarbonylamino groups are preferably aminocarbonylamino groups having 1 to 30 carbon atoms, examples of which include carbamoylamino, N,N-dimethylaminocarbonylamino, N,N-diethylaminocarbonylamino, or morpholinocarbonylamino. These may be either substituted or unsubstituted.

The alkoxycarbonylamino groups are preferably alkoxycarbonylamino groups having 2 to 30 carbon atoms, examples of which include methoxycarbonylamino, ethoxycarbonylamino, tert-butoxycarbonylamino, n-octadecyloxycarbonylamino, or N-methyl-methoxycarbonylamino. These may be either substituted or unsubstituted.

The aryloxycarbonylamino groups are preferably aryloxycarbonylamino groups having 7 to 30 carbon atoms, examples of which include phenoxycarbonylamino, p-chlorophenoxycarbonylamino, or m-(n-octyloxy)phenoxycarbonylamino. These may be either substituted or unsubstituted.

The alkyl- or aryl-sulfonylamino groups are preferably alkylsulfonylamino groups having 1 to 30 carbon atoms or arylsulfonylamino groups having 6 to 30 carbon atoms, examples of which include methylsulfonylamino, butylsulfonylamino, phenylslufonylamino, 2,3,5-trichlorophenylslufonylamino, or p-methylphenylsulfonylamino. These may be either substituted or unsubstituted.

The alkylthio groups are preferably alkylthio groups having 1 to 30 carbon atoms, examples of which include methylthio, ethylthio, or n-hexadecylthio. These may be either substituted or unsubstituted.

The arylthio groups are preferably arylthio groups having 6 to 30 carbon atoms, examples of which include phenylthio, p-chlorophenylthio, or m-methoxyphenylthio. These may be either substituted or unsubstituted.

The heterocyclic thio groups are preferably heterocyclic thio groups having 2 to 30 carbon atoms, examples of which include 2-benzothiazolylthio or 1-phenyltetrazol-5-ylthio. These may be either substituted or unsubstituted.

The sulfamoyl groups are preferably sulfamoyl groups having 0 to 30 carbon atoms, examples of which include N-ethylsulfamoyl, N-(3-dodecyloxypropyl)sulfamoyl, N,N-dimethylsulfamoyl, N-acetylsulfamoyl, N-benzoylsulfamoyl, or N-(N'-phenylcarbamoyl)sulfamoyl. These may be either substituted or unsubstituted.

The alkyl- or aryl-sulfinyl groups are preferably alkylsulfinyl groups having 1 to 30 carbon atoms or arylsulfinyl groups having 6 to 30 carbon atoms, examples of which include methylsulfinyl, ethylsulfinyl, phenylsulfinyl, or p-methylphenylslufinyl. These may be either substituted or unsubstituted.

The alkyl- or aryl-sulfonyl groups are preferably alkylsulfonyl groups having 1 to 30 carbon atoms or arylsulfonyl groups having 6 to 30 carbon atoms, examples of which include methylsulfonyl, ethylsulfonyl, phenylsulfonyl, or p-methylphenylslufonyl. These may be either substituted or unsubstituted.

The acyl groups are preferably formyl, alkylcarbonyl groups having 2 to 30 carbon atoms, arylcarbonyl groups having 7 to 30 carbon atoms, or heterocyclic carbonyl groups having 4 to 30 carbon atoms linked at a carbon atom to the carbonyl group, examples of which include acetyl, pivaloyl, 2-chloroacetyl, stearoyl, benzoyl, p-n-octyloxyphenylcarbonyl, 2-pyridylcarbonyl, or 2-furilcarbonyl. These may be either substituted or unsubstituted.

The aryloxycarbonyl groups are preferably aryloxycarbonyl groups having 7 to 30 carbon atoms, examples of which include phenoxycarbonyl, o-chlorophenoxycarbonyl, m-nitrophenoxycarbonyl, or p-tert-butylphenoxycarbonyl. These may be either substituted or unsubstituted.

The alkoxycarbonyl groups are preferably alkoxycarbonyl groups having 2 to 30 carbon atoms, examples of which include methoxycarbony, ethoxycarbony, tert-butoxycarbonyl, or n-octadecyloxycarbonyl. These may be either substituted or unsubstituted.

The aryl or heterocyclic azo groups are preferably arylazo groups having 6 to 30 carbon atoms or heterocyclic azo groups having 3 to 30 carbon atoms, examples of which include phenylazo, p-chlorophenylazo, or 5-ethylthio-1,3,4-thiadiazol-2-ylazo. These may be either substituted or unsubstituted.

The imido groups are preferably N-succinimido or N-phthalimido. These may be either substituted or unsubstituted.

The phosphino groups are preferably phosphino groups having 2 to 30 carbon atoms, examples of which include dimethylphosphino, diphenylphosphino, or methylphenoxyphosphino. These may be either substituted or unsubstituted.

The phosphinyl groups are preferably phosphinyl groups having 2 to 30 carbon atoms, examples of which include phosphinyl, dioctyloxyphosphinyl, or diethoxyphosphinyl. These may be either substituted or unsubstituted.

The phosphinyloxy groups are preferably phosphinyloxy groups having 2 to 30 carbon atoms, examples of which include diphenoxyphosphinyloxy or dioctyloxyphosphinyloxy. These may be either substituted or unsubstituted.

The phosphinylamino groups are phosphinylamino groups having 2 to 30 carbon atoms, examples of which include dimethoxyphosphinylamino or dimethylaminophosphinylamino. These may be either substituted or unsubstituted.

The silyl groups are preferably silyl groups having organic groups having 3 to 30 carbon atoms (alkyl groups and/or aryl groups), examples of which include trimethylsilyl, tert-butyldimethylsilyl, or phenyldimethylsilyl. These may be either substituted or unsubstituted.

In the substituent group R, substituents having a hydrogen atom may have lost a hydrogen atom and be substituted with the substituents mentioned above. Examples of such functional groups include alkylcarbonylaminosulfonyl groups, arylcarbonylaminosulfonyl groups, alkylsulfonylaminocarbonyl groups, or arylsulfonylaminocarbonyl groups. Examples thereof include a methylsulfonylaminocarbonyl group, a p-methylphenylslufonylaminocarbonyl group, an acetylaminosulfonyl group, or a benzoylaminosulfonyl group.

In Formula (1), preferred as $R^1$, $R^3$, $R^4$ and $R^7$ other than a liquid crystalline substituent is a hydrogen atom, an amino group, an alkylamino group, an arylamino group, a hydroxyl group, an alkoxy group, an aryloxy group, an acylamino group, a carbonyloxy group, an alkylthio group, or an arylthio group. More preferred is a hydrogen atom, a hydroxyl group, an amino group, an arylamino group, or an arylthio group.

In Formula (1), preferred as $R^2$ other than a liquid crystalline substituent is a hydrogen atom, a hydroxyl group, an amino group, an alkylamino group, an arylamino group, an alkoxy group, an aryloxy group, a carbamoyl group, an acylamino group, a carbonyloxy group, an alkylthio group, or an arylthio group. More preferred are a hydrogen atom, a halogen atom, or an alkyl group.

In Formula (1), preferred as $R^5$ other than a liquid crystalline substituent is a hydrogen atom, a halogen atom, an aryl group, a hydroxyl group, an amino group, an alkylamino group, an arylamino group, an alkoxy group, an aryloxy group, an acylamino group, a carbonyloxy group, an alkylthio group, or an arylthio group. More preferred are a hydrogen atom, a halogen atom, or an aryl group.

In Formula (1), preferred as $R^6$ other than a liquid crystalline substituent is a hydrogen atom, a halogen atom, an aryl group, a hydroxyl group, an amino group, an alkylamino group, an arylamino group, an alkoxy group, an aryloxy group, an acylamino group, a carbonyloxy group, an alkylthio group, or an arylthio group. More preferred are a hydrogen atom, a halogen atom, or an aryl group.

In Formula (1), if the dichroic dye has one or more liquid crystalline substituents, the number thereof is not particularly limited. The dichroic dye preferably has 1 to 4, and more preferably 1 or 2 liquid crystalline substituents.

Among $R^1$, $R^2$, $R^3$, $R^4$, $R^5$, $R^6$ or $R^7$ in Formula (1), the liquid crystalline substituent is preferably $R^3$, $R^4$, $R^5$, $R^6$, or $R^7$, and more preferably is $R^3$, $R^4$, $R^5$, or $R^7$.

When the dichroic dye has two liquid crystalline substituents in Formula (1), it is preferable that the dichroic dye have liquid crystalline substituents in the combination of $R^3$ and $R^7$, $R^5$ and $R^7$, $R^3$ and $R^4$, or $R^3$ and $R^5$.

When the dichroic dye has three liquid crystalline substituents in Formula (1), it is preferable that the dichroic dye have liquid crystalline substituents in the combination of $R^3$, $R^5$ and $R^7$, or $R^3$, $R^4$ and $R^7$.

Among $R^1$, $R^2$, $R^3$, $R^4$, $R^5$, $R^6$ or $R^7$ in Formula (1), the substituent which is not liquid crystalline is preferably $R^1$ or $R^2$, and more preferably is $R^2$.

A liquid crystalline substituent is a substituent having two or more cyclic structures, wherein the cyclic structure means an arylene group, a heteroarylene group or a divalent alicyclic hydrocarbon group.

The liquid crystalline substituent is preferably a substituent represented by the following Formula (5).

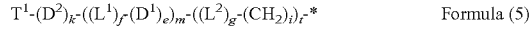

$$T^1-(D^2)_k-((L^1)_f-(D^1)_e)_m-((L^2)_g-(CH_2)_i)_t-* \quad \text{Formula (5)}$$

In Formula (5), * represent the linking site of $R^1$, $R^2$, $R^3$, $R^4$, $R^5$, $R^6$ or $R^7$ in Formula (1). $D^1$ and $D^2$ each independently represent an arylene group, a heteroarylene group, or a divalent alicyclic hydrocarbon group. $L^1$ and $L^2$ represent a bivalent linking group. $T^1$ represents an alkyl group, an alkoxy group, an alkoxycarbonyl group, an acyl group, an acyloxy group, a halogen atom, or a cyano group.

e represents an integer from 1 to 3; f represents an integer from 1 to 3; m represents an integer from 1 to 3; k represents 1 or 2; g represents 0 or 1; i represents an integer from 0 to 20; t represents an integer from 1 to 4. The total number of the groups represented by $D^1$ and $D^2$ is an integer from 2 to 5. When e is 2 or larger, two or more groups represented by $D^1$ may be the same or different; when k is 2 or larger, two or more groups represented by $D^2$ may be the same or different; when m is 2 or larger, two or more groups represented by $((L^1)_f-(D^1)_e)$ may be the same or different; and when f is 2 or larger, two or more groups represented by $L^1$ are respectively different linking groups. $(g+i) \times t$ represents an integer from 0 to 40; When t is 2 or larger, two or more groups represented by $((L^2)_g-(CH_2)_i)$ may be the same or different In Formula (5), the arylene groups represented by $D^1$ and $D^2$ are preferably arylene groups having 6 to 20 carbon atoms, and more preferably are arylene groups having 6 to 10 carbon atoms. Specific examples of preferable arylene groups include phenylene groups and naphthalene groups, e.g., a 1,4-phenylene group, a naphthalene-2,6-diyl group, and a tetrahydronaphthalene-2,6-diyl group.

In Formula (5), the heteroarylene groups represented by $D^1$ and $D^2$ are preferably heteroarylene groups having 1 to 20 carbon atoms, and more preferably are heteroarylene groups having 2 to 9 carbon atoms. Specific examples of preferable heteroarylene groups include groups composed of a pyridine ring, a quinoline ring, an isoquinoline ring, a pyrimidine ring, a pyrazine ring, a thiophene ring, a furan ring, an oxazole ring, a thiazole ring, an imidazole ring, a pyrazole ring, an oxadiazole ring, a thiadiazole ring or a triazole ring, or heteroarylene groups obtained by removal of one hydrogen atom from each of two carbon atoms of a condensed ring resulting from condensation of those rings.

In Formula (5), the divalent alicyclic hydrocarbon groups represented by $D^1$ and $D^2$ are preferably divalent alicyclic hydrocarbon groups having 3 to 20 carbon atoms, and more preferably are divalent alicyclic hydrocarbon groups having 4 to 12 carbon atoms. Specific examples of preferable divalent alicyclic hydrocarbon groups include a cyclohexanediyl group, a decahydronaphthalenediyl group, a spiro[5.5]undecylene group, and more preferably examples are a cycrohexane-1,4-diyl group, a decahydronaphthalene-2,6-diyl group, or a 3,9-spiro[5.5]undecylene group.

In Formula (5), the arylene groups, the heteroarylene groups, and the divalent alicyclic hydrocarbon groups which represent $D^1$ and $D^2$ may be either substituted or unsubstituted. In Formula (5), when e, m, or k is 2 or greater, a plurality of $D^1$'s and $D^2$'s each independently may have a substituent. They may have the same substituents, different substituents, or no substitutes.

Substituents preferable as substituents of the divalent arylene group, the divalent heteroarylene group and the divalent alicyclic hydrocarbon group represented by $D^1$ and $D^2$ are alkyl groups, alkoxy groups, halogen atoms, or a cyano group.

In Formula (5), $L^1$ represents a divalent linking group. It preferably is an alkanediyl group, an alkenylene group, an alkynylene group, an ether group, an ester group (—COO—, —OCO—), a carbonyl group, an azo group (—CH=N—, —N=CH—), an azoxy group, or an alkyleneoxy group, and it more preferably is an alkanediyl group (e.g., ethylene group), an alkynylene group (e.g, ethynylene group), an ester group, or an alkyleneoxy group (e.g., methyleneoxy group).

In Formula (5), $T^1$ represents an alkyl group, an alkoxy group, an alkoxycarbonyl group, an acyl group, an acyloxy group, a halogen atom, or a cyano group.

$T^1$ is preferably an alkyl group having 1 to 30 carbon atoms, more preferably 3 to 20 carbon atoms, and furthermore preferably 3 to 10 carbon atoms (for example, n-propyl group, n-butyl group, n-pentyl, n-hexyl group, hydroxymethyl, trifluoromethyl, benzyl, carboxyethyl, ethoxycarbonylmethyl, acetylaminomethyl, where unsaturated hydrocarbon groups having 2 to 18 carbon atoms, preferably 3 to 10 carbon atoms (for example, vinyl group, ethynyl group, 1-cyclohexenyl group, benzylidyne group, or benzyldiene group) are included in substituted alkyl groups); an alkoxy group having 1 to 30 carbon atoms, more preferably 3 to 20 carbon atoms, and furthermore preferably 3 to 10 carbon atoms (for example, n-propyloxy group, n-butoxy group, n-pentyloxy group, or n-hexyloxy group); or a halogen atom (for example, fluorine atom or chlorine atom).

The alkyl groups, the alkoxy groups, the alkoxycarbonyl groups, the acyl groups and the acyloxy groups represented by $T^1$ in Formula (5) may either have or not have a substituent. Examples of the substituent are those of the aforementioned substituent group R.

The substituent of the alkyl group, the alkoxy group, the alkoxycarbonyl group, the acyl group and the acyloxy groups represented by $T^1$ is preferably a halogen atom (especially, chlorine atom or fluorine atom), a cyano group, a hydroxy group, an alkoxy group or an acyl group.

In Formula (5), e represents an integer from 1 to 3, and preferably 1 or 2. When e is 2 or 3, two or more groups represented by $D^1$ may be the same or different.

In Formula (5), m represents an integer from 1 to 3, and preferably 1 or 2. When m is 2 or 3, two or more groups represented by $D^1$ may be the same or different, and two or more groups represented by $L^1$ may be the same or different.

In Formula (5), k represents 1 or 2, when k is 2, two or more groups represented by $D^2$ may be the same or different.

In Formula (5), f represents an integer from 0 to 3, and preferably from 0 to 2. When f is 2 or 3, two or more groups represented by $L^1$ are respectively different linking groups.

In Formula (5), the total number of the groups represented by $D^1$ and $D^2$, that is, exm+k is an integer from 2 to 5, more preferably an integer from 2 to 4, furthermore preferably 2 or 3. when e is 2 or larger; two or more groups represented by $D^1$ may be the same or different; when k is 2 or larger, two or more groups represented by $D^2$ may be the same or different; when m is 2 or larger, two or more groups represented by $(L^1)_f$-$(D^1)_e$ may be the same or different.

Preferable combinations of e, f, m, and k will be described as follows.

(I) e=1, f=0, m=1, k=1
(II) e=1, f=2, m=1, k=1
(III) e=2, f=0, m=1, k=1
(IV) e=1, f=0, m=1, k=2
(V) e=1, f=2, m=1, k=2
(VI) e=1, f=1, m=1, k=1
(VII) e=2, f=2, m=1, k=1

In Formula (5), $L^2$ represents a divalent linking group, and preferably is an ether group, a thioether group, an ester group (—COO—, —OCO—), or a carbonyl group.

In Formula (5), g represents 0 or 1; when g is 2 or larger; two or more groups represented by $L^2$ are respectively different linking groups.

In Formula (5), i represents an integer from 0 to 20, and preferably an integer from 0 to 11.

In Formula (5), t represents an integer from 1 to 4, and preferably an integer from 1 to 3. When t is 2 or larger; two or more groups represented by $((L^2)_g$-$(CH_2)_i)$ may be the same or different, and plural i may be the same or different.

Herein, (g+i)×t represents an integer from 0 to 40, preferably an integer from 0 to 30, and more preferably an integer from 0 to 20.

In Formula (1), n represents 0 or 1 and preferably 1.

In Formula (1), X and Y independently represent an alkyl group, a halogen atom, an alkoxy group, or an alkylthio group, preferably an alkyl group or a chlorine atom, more preferably an alkyl group, furthermore preferably an alkyl group having from 1 to 20 carbon atoms, and particularly preferably a methyl group.

In Formula (1), Z is an alkyl group having 3 or more carbon atoms, an acyl group, or an aryl group. The alkyl group and the aryl group which are represented by Z may have lost a hydrogen atom and have been substituted with a substituent of the substituent group R.

Z in Formula (1) is preferably an alkyl group having 3 or more carbon atoms, and more preferably, from the viewpoint of improvement in solubility due to steric hindrance and a high order parameter due to the highly rod-like in the longitudinal direction, more preferably an alkyl group having from 3 to 40 carbon atoms.

The alkyl group having 3 or more carbon atoms which is represented by Z may be straight chained, branched or cyclic. One preferable embodiment of Z in Formula (1) is an alkyl group represented by the following Structural Formula (A).

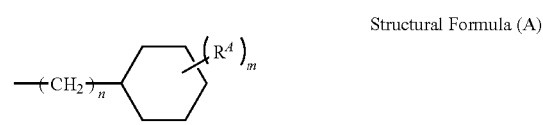

Structural Formula (A)

In Structural Formula (A), n represents an integer from 0 to 40, preferably an integer from 0 to 30, and more preferably an integer from 0 to 20.

m represents an integer from 0 to 5, preferably an integer from 0 to 3, and more preferably 1.

$R^A$ represents a substituent of the aforementioned substituent group R. It is preferably an alkyl group, an alkoxy group, an alkylthio group, or an acyl group, and more preferably is an alkyl group having 1 to 30 carbon atoms, and furthermore preferably is an alkyl group having 1 to 20 carbon atoms.

The alkyl group represented by Structural Formula (A) is preferably an alkyl group represented by Structural Formula (B).

Structural Formula (B)

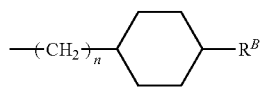

In Structural Formula (B), n is synonymous with the n in the aforementioned Structural Formula (A). $R^B$ represents an alkyl group having 1 to 30 carbon atoms and it is preferably an alkyl group having 1 to 20 carbon atoms.

The acyl group represented by Z in Formula (1), it is preferable that an alkoxy group or an alkyl group be linked thereto.

The alkoxy group linked to the acyl group represented by Z is preferably an alkoxy group having 1 to 20 carbon atoms, and it specifically is a cyclohexyloxy group, a trans-n-pentyl-cyclohexyloxy group, a n-octyloxy group, or the like.

The alkyl group linked to the acyl group represented by Z is preferably an alkyl group having 1 to 20 carbon atoms, and it specifically is a cyclohexyl group, a trans-n-butylcyclo-hexyl group, a n-octyl group, or the like.

The aryl group represented by Z is preferably a phenyl group, and it is preferable that the phenyl group be substituted with an alkyl group or an alkoxy group. While the substitution position where the phenyl group is substituted is not particularly restricted, 2-position and 3-position are preferred.

The alkyl group with which the phenyl group is substituted is preferably an alkyl group having 1 to 30 carbon atoms, specifically, a n-butyl group, a n-octyl group, an iso-pentyl, a cyclohexyl group, or the like.

The alkoxy group with which the phenyl group is substituted is preferably an alkoxy group having 1 to 30 carbon atoms, specifically, a n-butoxy group, a n-octyloxy group, a cyclohexyloxy group, or the like.

In Formula (1), A is an oxygen atom, a sulfur atom or a nitrogen atom, and preferably is an oxygen atom. That is, the compound represented by Formula (1) is preferably a compound represented by the following Formula (2).

Formula (2)

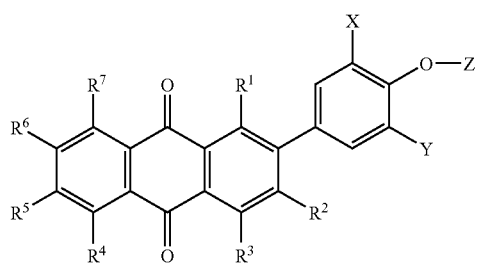

In Formula (2), at least one among $R^1, R^2, R^3, R^4, R^5, R^6$ or $R^7$ is a liquid crystalline substituent, and those among $R^1, R^2,$ $R^3, R^4, R^5, R^6$ and $R^7$ that are not the liquid crystalline substituent each independently represent a hydrogen atom or a substituent. X and Y each independently represent an alkyl group, a halogen atom, an alkoxy group, or an alkylthio group. Z represents an alkyl group having 3 or more carbon atoms, an acyl group, or an aryl group.

$R^1, R^2, R^3, R^4, R^5, R^6, R^7, X, Y,$ and Z are synonymous with $R^1, R^2, R^3, R^4, R^5, R^6, R^7,$ X, Y, and Z in Formula (1), respectively.

Among the compounds represented by Formula (1), more preferable embodiments include compounds represented by the following Formula (3) or Formula (4).

Formula (3)

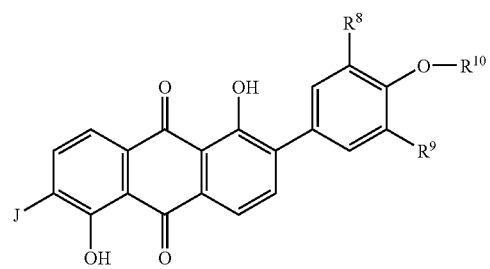

Formula (4)

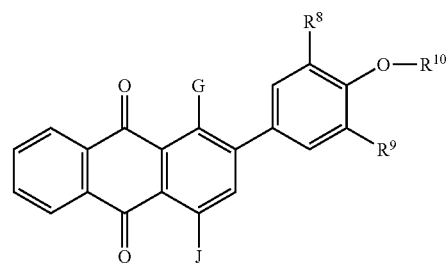

$R^8$ and $R^9$ in Formulas (3) and (4) each independently represent an alkyl group. They are each preferably an alkyl group having 1 to 20 carbon atoms, and more preferably a methyl group.

$R^{10}$ represents an alkyl group having 3 or more carbon atoms. Preferred are the alkyl groups having 3 or more carbon atoms which were described for Z in Formula (1). The preferable range is also the same.

J represents a liquid crystalline substituent. The liquid crystalline substituent is synonymous with the liquid crystalline substituent in Formula (1).

G represents a hydroxyl group or an amino group. The amino group may be any of a primary amino group, a secondary amino group, and a tertiary amino group, and it is preferably a primary amino group.

Specific examples of compounds represented by Formula (1) (including Formulas (2) to (4)) are shown below, but the present invention is not limited to them.

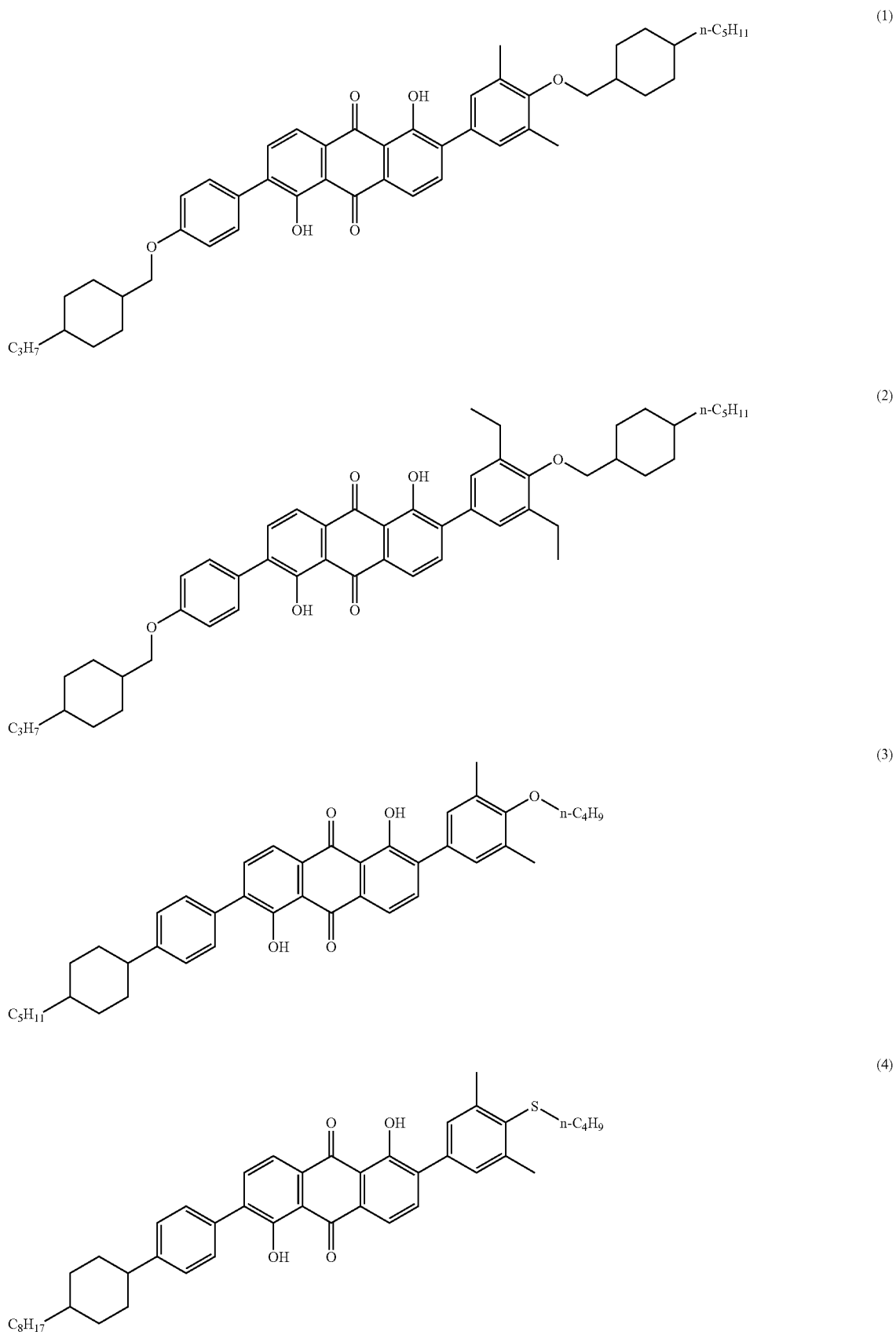

-continued
(5)
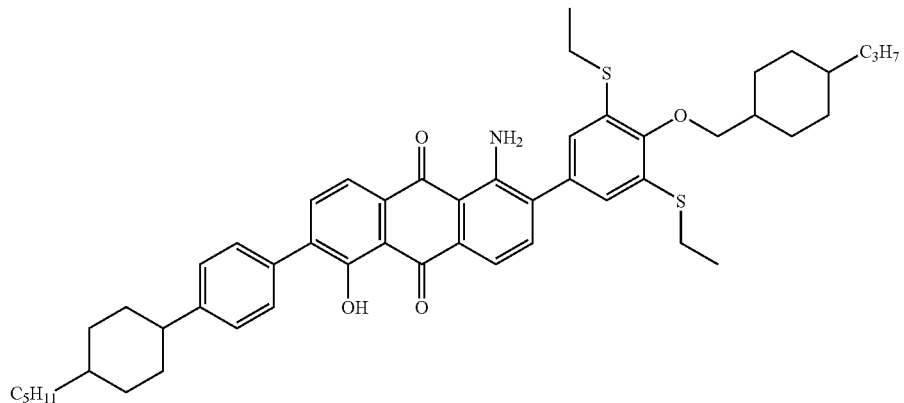
(6)
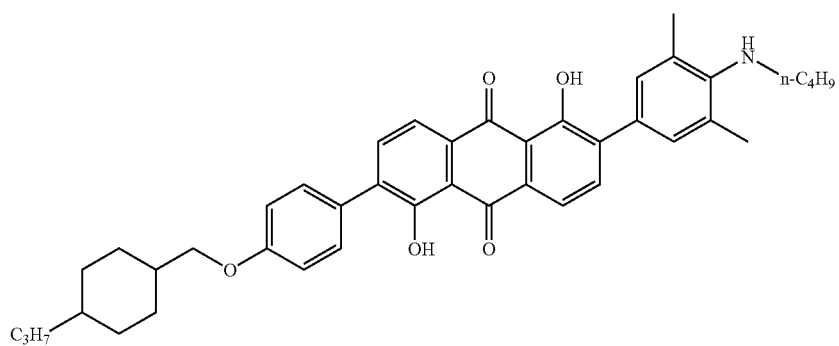
(7)
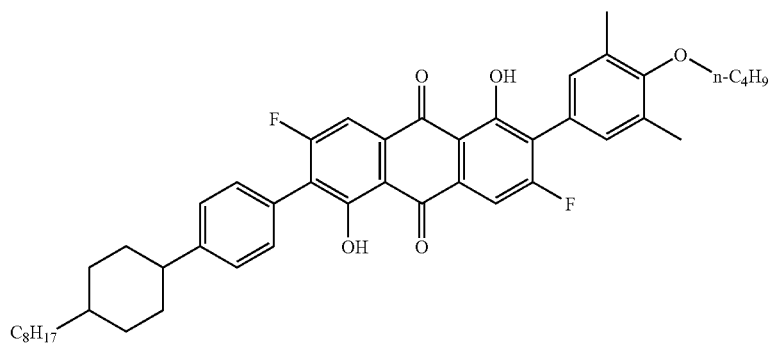
(8)
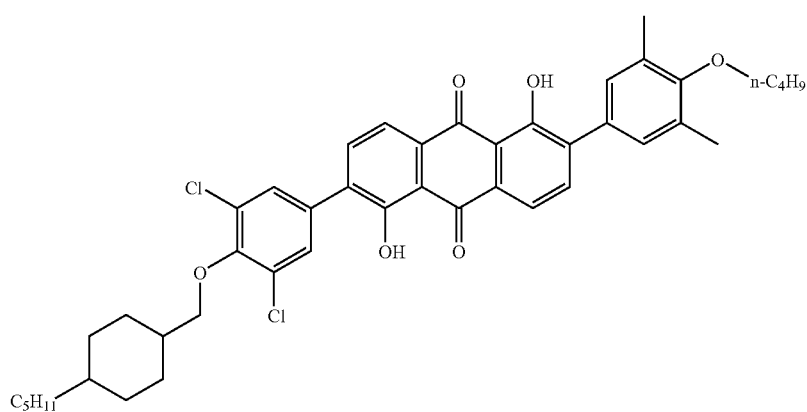

-continued
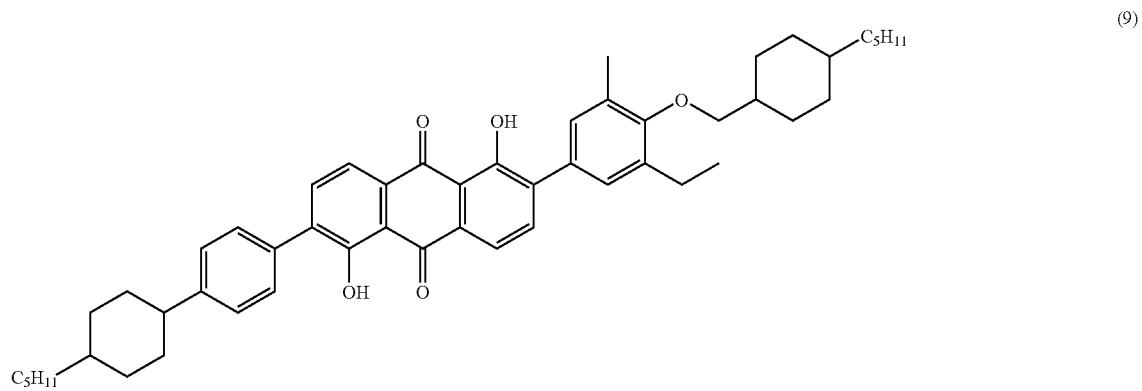
(9)
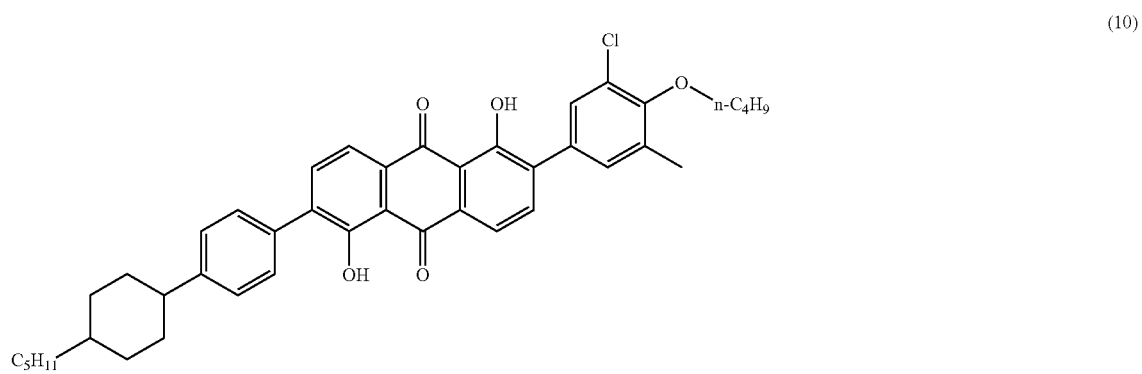
(10)
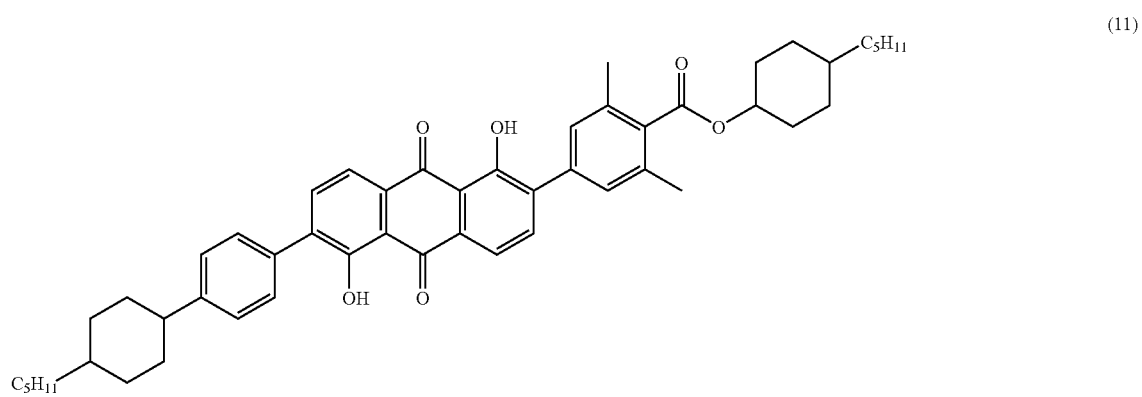
(11)
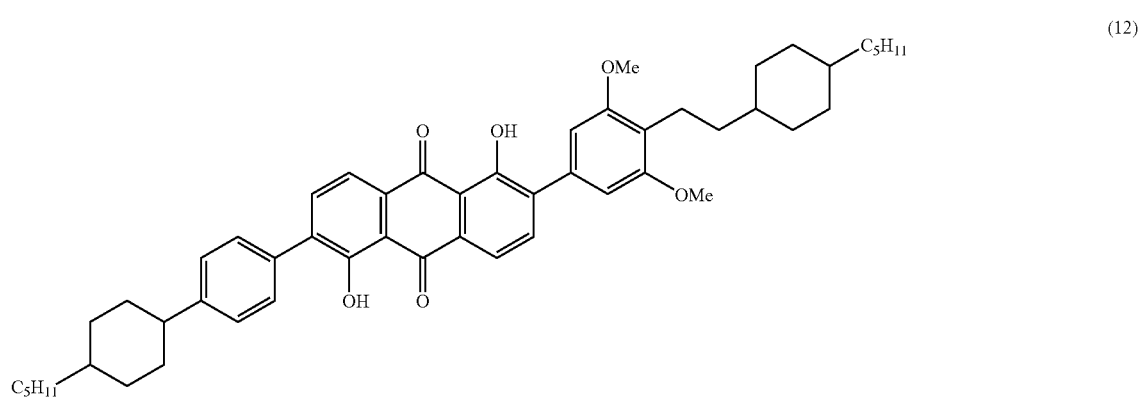
(12)

-continued
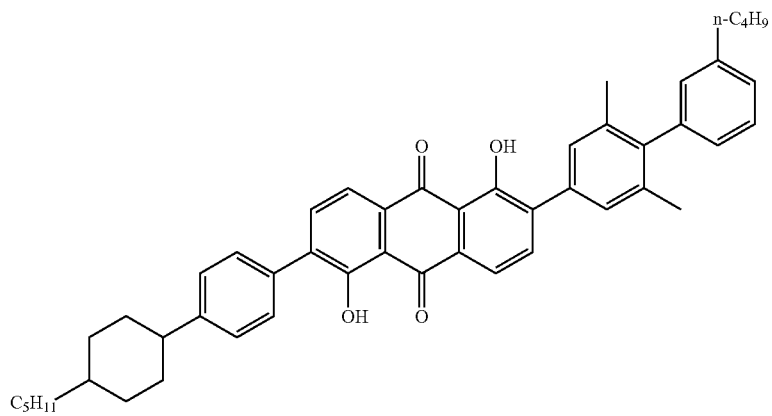
(13)
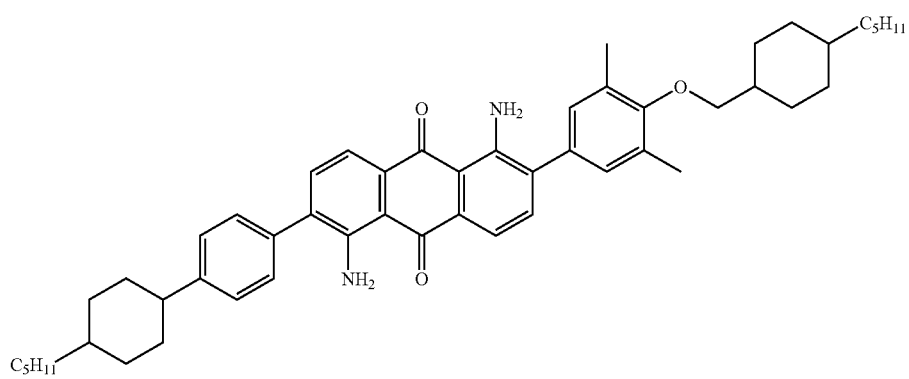
(14)
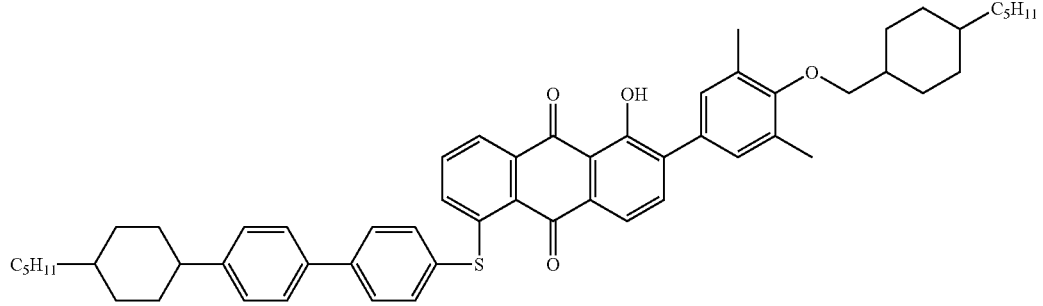
(15)
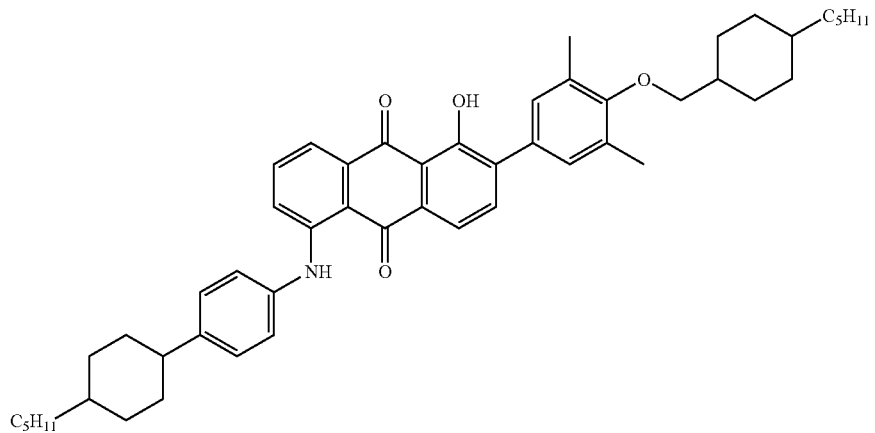
(16)

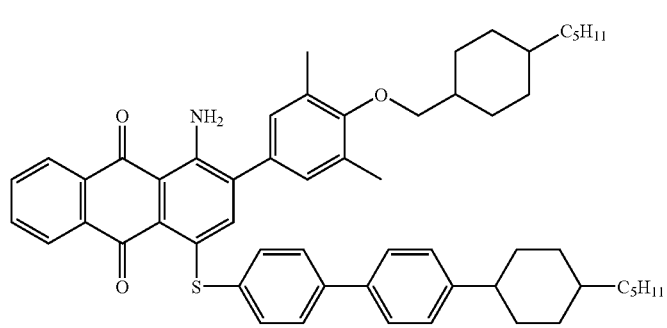
(17)
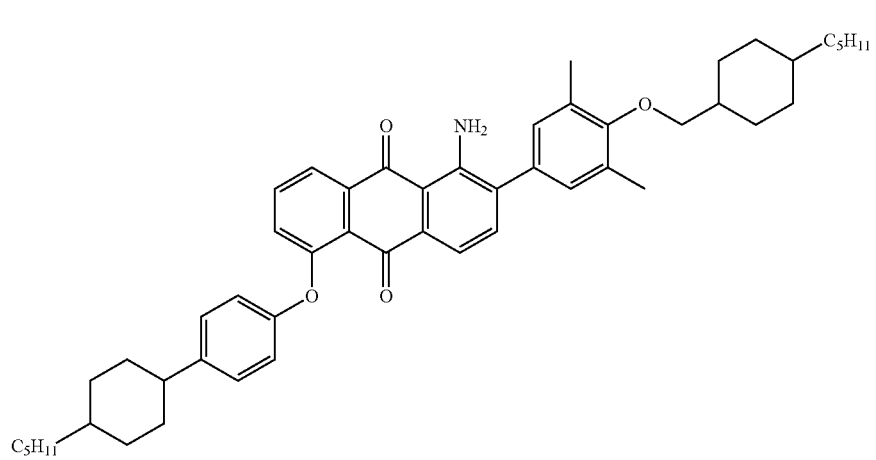
(18)
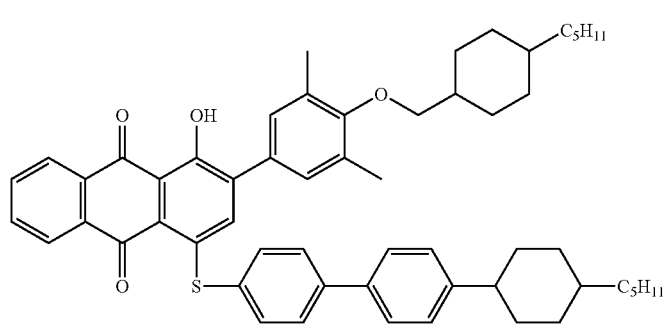
(19)
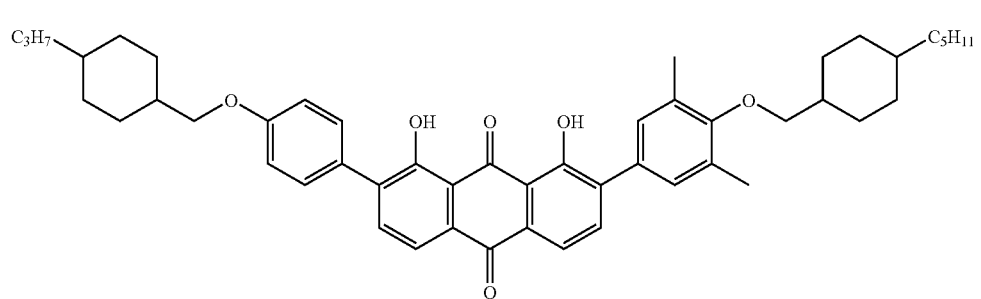
(20)

-continued
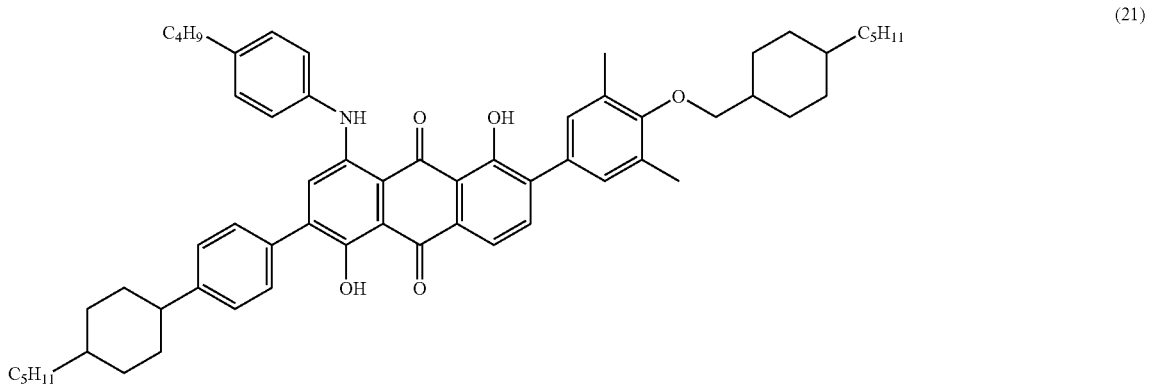
(21)
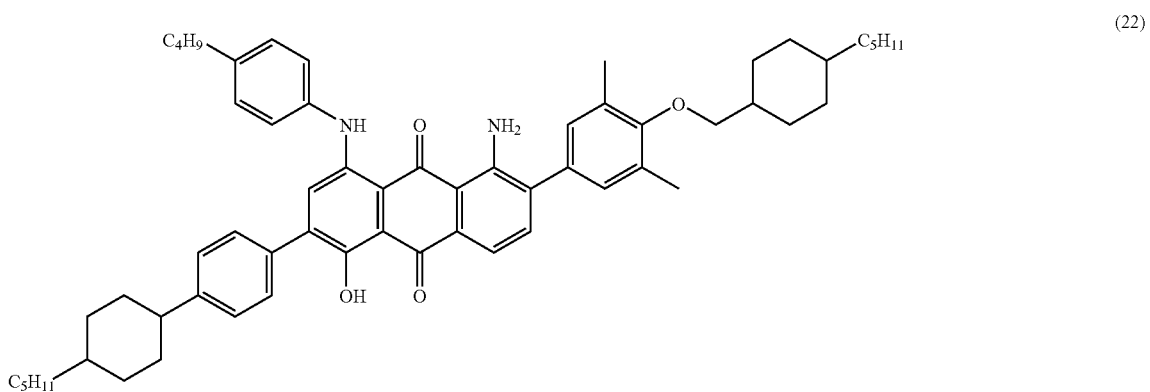
(22)
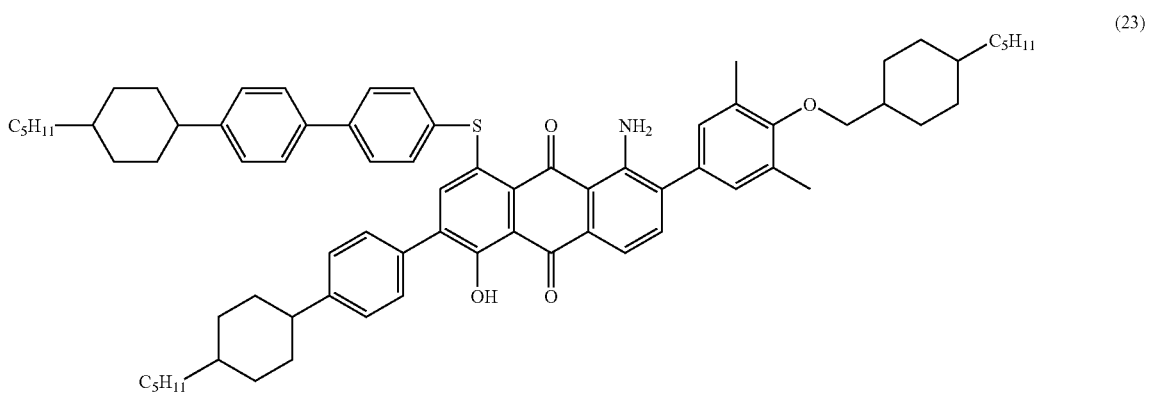
(23)
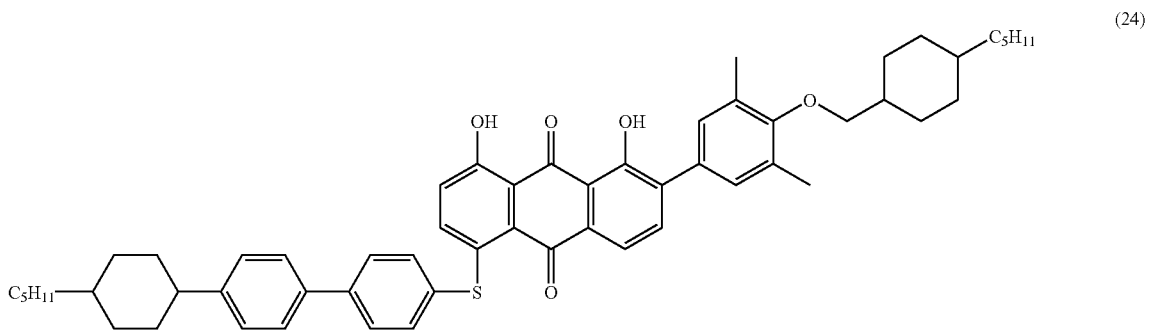
(24)

-continued
(25)
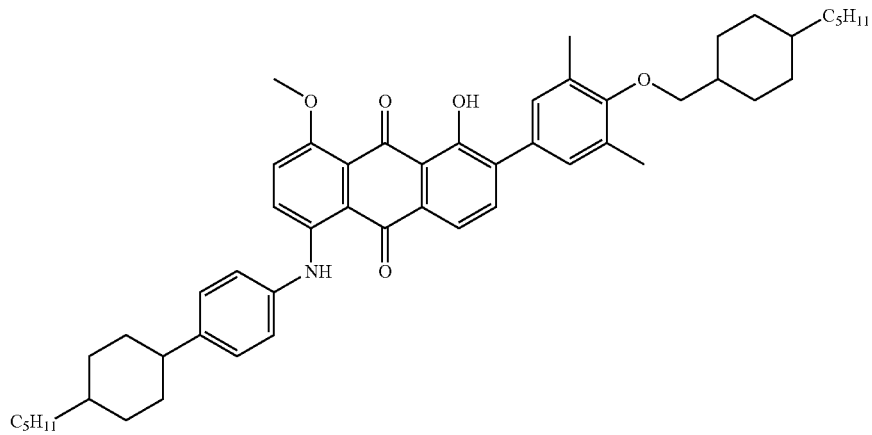
(26)
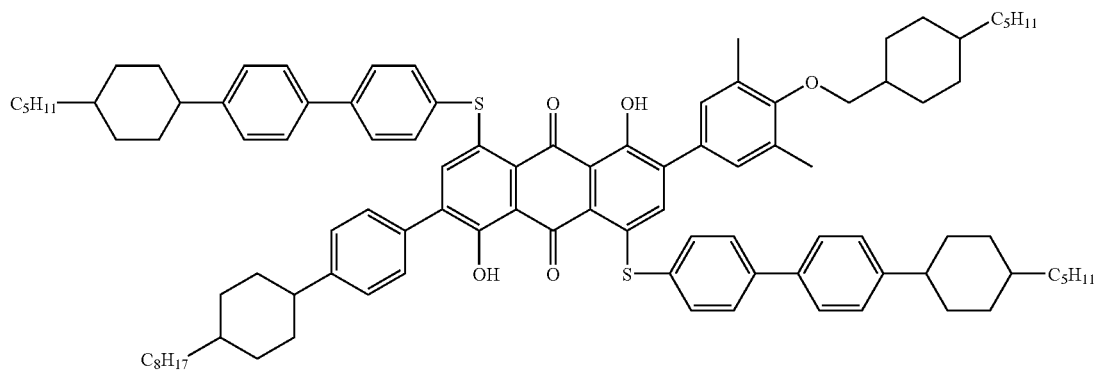
(27)
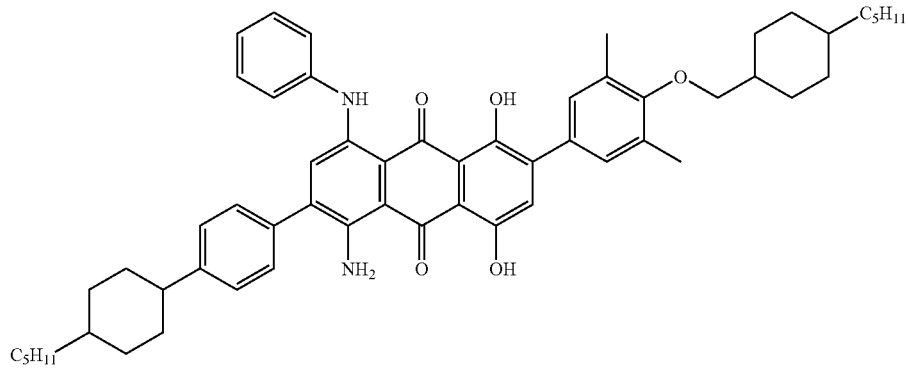
(28)
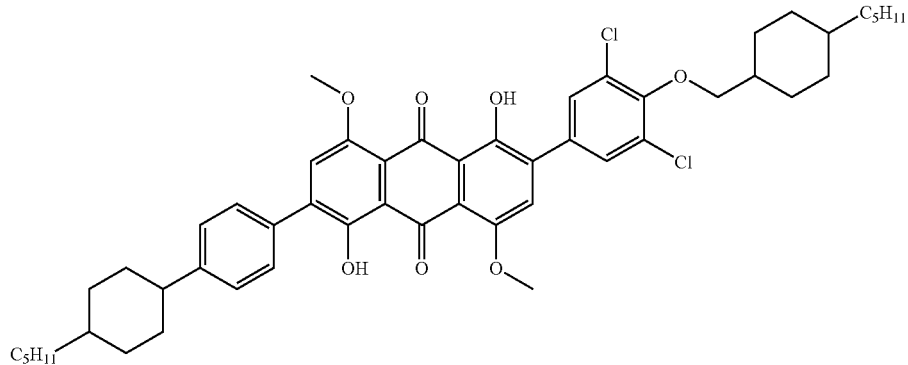

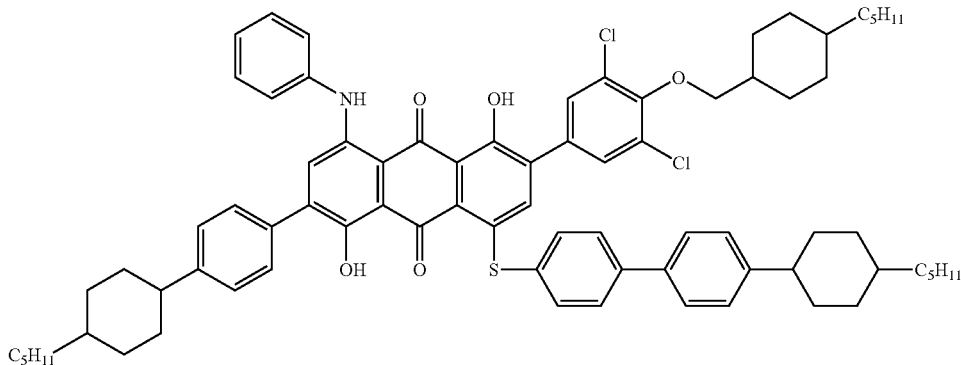
(29)

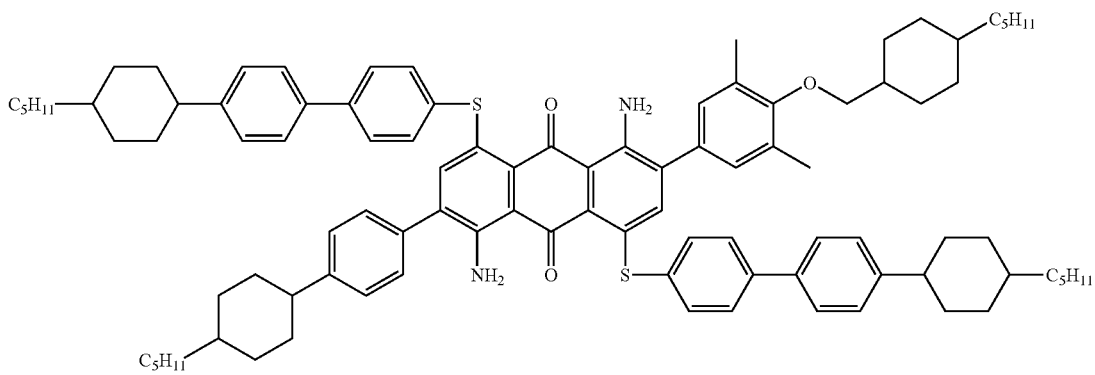
(30)

The compound represented by the Formula (1) can be synthesized in accordance with conventional synthesis methods. The conventional synthesis methods are described in, for example, JP-A No. 2003-192664, and Galevskaya, T. P., Moroz, A. A., Myasnikova, R. N., and Shvartsberg. M. S., Zhurnal Organicheskoi Khimii, 1988, 24(2), 405. The specific compounds (1) to (30) can be synthesized with reference to these documents.

The dichroic dye to be used for the liquid crystal composition of the present invention may be used alone, and a mixture of two or more dichroic dyes may be used. When two or more dyes are mixed, dyes of the present invention may be mixed, or alternatively a dye of the present invention and conventional dichroic dyes may be mixed together. Examples of such conventional dichroic dyes include those disclosed in A. V. Ivashchenko, Diachronic Dyes for Liquid Crystal Display, CRC, 1994. For black color display, it is necessary to absorb all light in the visible range and it is preferable to mix two or more dichroic dyes.

(Liquid Crystal)

There is no specific limitation on the liquid crystal available for the liquid crystal composition of the present invention. For example, liquid crystal composition which exhibit nematic phase or smectic phase can be used. Specific examples thereof include azomethine compounds, cyanobiphenyl compounds, cyanophenyl esters, fluorine-substituted phenyl esters, cyclohexanecarboxylic acid phenyl esters, fluorine-substituted cyclohexanecarboxylic acid phenyl esters, cyanophenylcyclohexane, fluorine-substituted phenylcyclohexane, cyano-substituted phenylpyrimidine, fluorine-substituted phenylpyrimidine, alkoxy-substituted phenylpyrimidine, fluorine-substituted alkoxy-substituted phenylpyrimidine, phenyldioxane, tolan compounds, fluorine-substituted tolan compounds, and alkenylcyclohexyl-benzonitrile. Detailed disclosure is in "Ekisho Debaisu Handobukku (Liquid Crystal Device Handbook)" edited by No. 142 Committee of Japan Society for the Promotion of Science, published by Nikkan Kogyo Shimbun Ltd., 1989, pages 154 to 192 and 715 to 722. Host liquid crystals substituted with fluorine which are suitable for TFT driving can also be used.

The liquid crystal composition of the present invention may be added with a compound showing no liquid crystalline property in order to change physical properties of the liquid crystal (e.g., the temperature range in which the liquid crystal phase appears). Moreover, compounds such as chiral compounds, UV absorbers and antioxidants may be contained. Examples of such additives include chiral reagents for TN and STN disclosed in "Ekisho Debaisu Handobukku (Liquid Crystal Device Handbook)", edited by No. 142 Committee of Japan Society for the Promotion of Science, published by Nikkan Kogyo Shimbun Ltd., 1989, pages 199 to 202.

While the ratio of the dichroic dye to the liquid crystal in the liquid crystal composition of the present invention may be any ratio, it is preferably from 0.1% by weight to 15% by weight and more preferably from 3% by weight to 8% by weight.

The dissolution of the dichroic dye to the liquid crystal can be attained with the aid of mechanical stirring, heating, ultrasonic vibration, or combinations thereof.

<Liquid Crystal Device>

The liquid crystal device of the present invention can be formed by disposing a liquid crystal layer containing the aforesaid liquid crystal composition between a pair of electrodes at least one of which is a transparent electrode.

As the electrode substrate to be used for the liquid crystal device of the present invention, a glass substrate or a plastic substrate is usually used. Examples of the plastic substrate include acrylic resins, polycarbonate resins and epoxy resins. Specific examples include triacetyl cellulose (TAC), polyethylene terephthalate (PET), polyethylene naphthalate (PEN), syndiotactic polystyrene (SPS), polyphenylene sulfide (PPS), polycarbonate (PC), polyarylate (PAr), polysulfone (PSF), polyester sulfone (PES), polyetherimide (PEI), cyclic polyolefin, and polyimide (PI). Preferred is polyethylene terephthalate (PET).

The thickness of the plastic substrate is not particularly limited, and it is from 30 μm to 700 μm, more preferably from 40 μm to 200 μm, and furthermore preferably from 50 μm to 150 μm. In any cases, the haze is preferably 3% or less, more preferably 2% or less, and furthermore preferably 1% or less. The total light transmittance is preferably 70% or more, more preferably 80% or more, and furthermore preferably 90% or more.

Resin modifiers such as plasticizers, dyes, pigments, antistatic agents, UV absorbers, antioxidants, inorganic fine particles, peeling accelerator, leveling agents and lubricants may, according to necessity, be added to the plastic substrate unless the effect of the present invention is affected.

The plastic substrates may be either light permeable or light impermeable. When a light impermeable support is used as the support, a white support having light reflectivity may be used. Examples of the white substrate include plastic substrates containing inorganic pigments such as titanium oxide or zinc oxide. In the case that the displaying surface is formed by the substrate, the substrate is required to have light permeability to at least the light in the visible range.

Detailed description about substrates is made, for example, in "Ekisho Debaisu Handobukka (Liquid Crystal Device Handbook)", edited by No. 142 Committee of Japan Society for the Promotion of Science, published by the Nikkan Kogyo Shimbun, Ltd., 1989, pages 218 to 231. On the substrate, an electrode layer preferably a transparent electrode, is formed. As the electrode layer, indium oxide, indium tin oxide (ITO), tin oxide, or the like can be used. For example, electrodes disclosed in "Ekisho Debaisu Handobukku (Liquid Crystal Device Handbook))", edited by No. 142 Committee of Japan Society for the Promotion of Science, published by the Nikkan Kogyo Shimbun, Ltd., 1989, pages 232 to 239 are used as the transparent electrode.

The liquid crystal device of the present invention is preferably provided with a layer subjected to an alignment process for the purpose of aligning the liquid crystal, on a surface of the substrate in contact with the liquid crystal. Such alignment process may be a process including applying and aligning a quaternary ammonium salt, a process including applying polyimide and rubbing it to align, a process including vapor depositing $SiO_x$ from an oblique direction, or an alignment process by light irradiation utilizing photoisomerization. For example, alignment films disclosed in "Ekisho Debaisu Handobukku (Liquid Crystal Device Handbook)", edited by No. 142 Committee of Japan Society for the Promotion of Science, published by the Nikkan Kogyo Shimbun, Ltd., 1989, pages 240 to 256 are used as the alignment film.

In the liquid crystal device of the present invention, it is permissible to form a gap of from 1 μm to 50 μm between the substrates with a spacer or the like and inject the liquid crystal composition into the space. For example, spacers disclosed in "Ekisho Debaisu Handobukku (Liquid Crystal Device Handbook)", edited by No. 142 Committee of Japan Society for the Promotion of Science, published by the Nikkan Kogyo Shimbun, Ltd., 1989, pages 257 to 262 are used as the spacer.

The liquid crystal device of the present invention may be driven by a simple matrix driving system, or by an active matrix driving system utilizing a thin film transistor (TFT) or the like. For example, driving systems disclosed in "Ekisho Debaisu Handobukku (Liquid Crystal Device Handbook)", edited by No. 142 Committee of Japan Society for the Promotion of Science, published by the Nikkan Kogyo Shimbun, Ltd., 1989, pages 387 to 460 are used as the driving system.

<Reflection Display Material, Light Modulating Material>

Because the liquid crystal device of the present invention can exert high display performance and high light modulating performance, it can be used suitably as reflection display materials, light modulating material, security, interior design, advertisement, and information display boards.

When the liquid crystal device is used as a reflection display material, it is required only that at least one of the pair of electrode substrates be a transparent electrode. A liquid crystal layer containing the aforementioned liquid crystal composition is formed between the pair of electrodes, and a light reflector is further formed. In a reflection display material, the light which entered from the observer side will be reflected by the light reflector, and an observer will observe the reflected light.

In addition, in a reflection display material, conventional components, such as a phase retarder, may optionally be provided.

When the liquid crystal device is used as a light modulating material, both the pair of electrode substrates are transparent. In a light modulating material, the light entered from the side opposite to an observer is observed from the opposite side via the light modulating material.

Because a light modulating material is sometimes used outdoors, it is preferable to provide a barrier film, a UV absorbing layer, an antireflection layer, a hard coat layer, an antismudging layer, a UV absorption layer, or the like.

The liquid crystal display using the liquid crystal device of the present invention may be in any system, examples of available systems include (1) homogeneous alignment and (2) homeotropic alignment, both being classified in the guest-host system described in "Ekisho Debaisu Handobukku (Liquid Crystal Device Handbook)", edited by No. 142 Committee of Japan Society for the Promotion of Science, published by the Nikkan Kogyo Shimbun, Ltd., 1989, page 309; (3) focalconic alignment and (4) homeotropic alignment, both being classified in White-Taylor type (phase transition); (5) combination with Super Twisted Nematic (STN); (6) combination with ferroelectric liquid crystal (FLC); and (1) Heilmeier type GH mode, (2) quarter-wave plate type GH mode, (3) double layer type GH mode, (4) phase transition type GH mode, and (5) polymer-dispersed liquid crystal (PDLC) type GH mode disclosed in "Hansha-gata Kara LCD Sogo Gijutsu (General Technologies of Reflection-type Color LCD)", supervised by Tatsuo Uchida, published by CMC, 1999, Chapter 2-1 "GH-mode, Reflective Type Color LCD", pages 15 to 16.

The liquid crystal device of the present invention can be used for the layered GH mode disclosed in JP-A Nos. 10-67990, 10-239702, 10-133223, 10-339881, 11-52411, 11-64880, 2000-221538, or the like, and for the GH mode utilizing microcapsules disclosed in JP-A No. 11-24090, or the like. It can be used also for reflection liquid crystal display materials such as those disclosed in JP-A Nos. 6-235931, 6-235940, 6-265859, 7-56174, 9-146124, 9-197388, 10-20346, 10-31207, 10-31216, 10-31231, 10-31232, 10-31233, 10-31234, 10-82986, 10-90674, 10-111513, 10-111523, 10-123509, 10-123510, 10-206851, 10-253993, 10-268300, 11-149252, 2000-2874, or the like. It can be used also for the polymer-dispersed liquid crystal type GH mode disclosed in JP-A Nos. 5-61025, 5-265053, 6-3691, 6-23061, 5-203940, 6-242423, 6-289376, 8-278490, and 9-813174.
EXAMPLES
Examples are hereinafter provided in order to describe the present invention in more detail, but the present invention is not limited to the Examples.
Example 1
Synthesis of Compound Example (1)
Compound example (1) was synthesized in accordance with the following scheme.
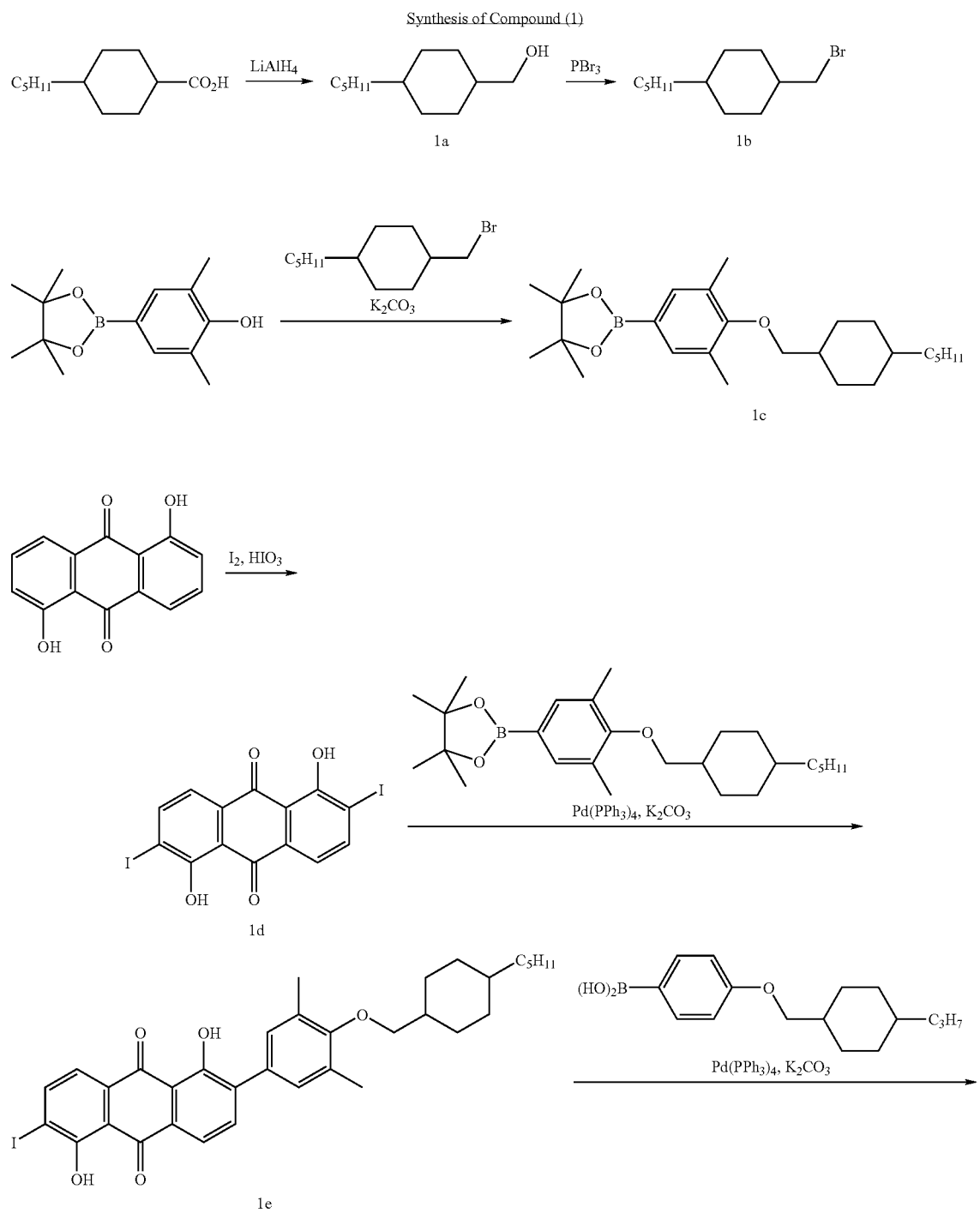

-continued

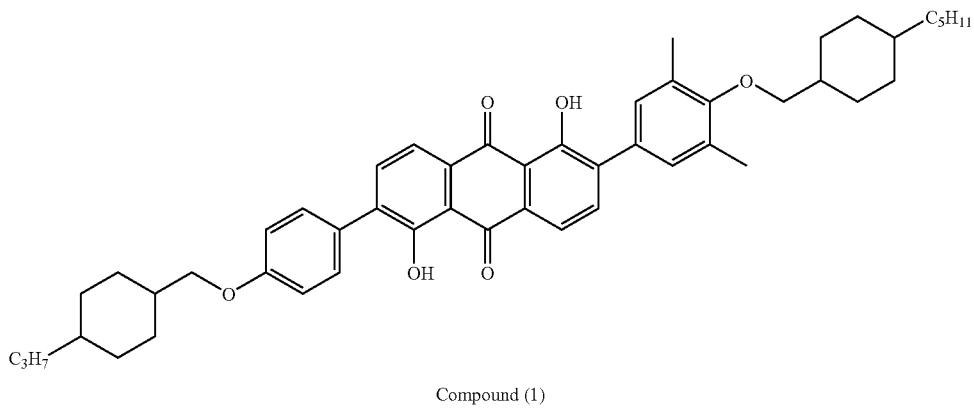

Compound (1)

(Synthesis of Compound 1a)

Under ice cooling, a THF solution (50 ml) including trans-4-pentylcyclohexanecarboxylic acid (15.9 g) was dropped into a 1 M THF solution (100 ml) containing LAH. After the dropping, the mixture was heated slowly and was stirred under reflux for 9 hours. After the completion of the reaction, the reaction solution was cooled at rest and then was dropped slowly into a mixture of ice and 1 N aqueous hydrochloric acid under stirring. Ethyl acetate was added thereto and the resulting organic layer was dried over sodium sulfate, followed by concentration under reduced pressure. The concentrate was subjected to vacuum distillation to yield Compound 1a (12.4 g).

(Synthesis of Compound 1b)

Compound 1a (12.0 g) was dissolved in dehydrated acetonitrile (230 ml), and phosphorus tribromide (13.5 ml) was added thereto, followed by stirring at 60° C. for 2.5 hours. After being cooled at rest, the mixture was poured into ice, followed by addition of ethyl acetate and subsequent extraction. The resulting organic layer was dried over sodium sulfate, followed by concentration under reduced pressure. The residue was subjected to silica gel column chromatographic purification (developing solvent: n-hexane) to yield Compound 1b (12.9 g).

(Synthesis of Compound 1c)

Compound 1b (8.0 g), 4-hydroxy-3,5-dimethylphenyl borate (8.0 g), and potassium carbonate (8.9 g) were added to dehydrate N-methylpyrrolidone, and the mixture was heated to 120° C. After stirring for 1 hour, the mixture was cooled at rest and 1 N aqueous hydrochloric acid and ethyl acetate were added thereto. The organic layer was washed with 1N aqueous hydrochloric acid twice, and then was dried over sodium sulfate, followed by concentration under reduced pressure. The residue was subjected to silica gel column chromatographic purification (developing solvent: n-hexane/ethyl acetate=9/1) to yield Compound 1c (6.9 g).

(Synthesis of Compound 1d)

To acetic acid (200 ml), 1,5-dihydroxyanthraquinone (5.0 g), iodine (16.9 g) and iodic acid (5.9 g) were added, and the mixture was heated to 110° C. and stirred for 2 hours. Water was added to the reaction solution, followed by collection of formed crystals by filtration. The crystals were washed with methanol and n-hexane to yield Compound 1d (6.3 g).

(Synthesis of Compound 1e)

To a solution of Compound 1d (2.0 g) and Compound 1c (2.0 g) in toluene (100 ml)/H$_2$O (50 ml), tetrakis(triphenylphosphine)palladium (0.09 g) and potassium carbonate (3.4 g) were added, followed by stirring under reflux for 18 hours. After cooling at rest, 1 N aqueous hydrochloric acid/chloroform was added thereto and the resulting organic layer was dried over sodium sulfate, followed by concentration under reduced pressure. The residue was subjected to silica gel column chromatographic purification (developing solvent: chloroform/n-hexane=7/3) to yield Compound 1e (0.8 g).

(Synthesis of Exemplary Compound (1))

To a solution of Compound 1e (100 mg) and 4-(4-n-propylcyclohexylmethyleneoxy)phenylboric acid (56 mg) in toluene (5 ml)/H$_2$O (2.5 ml), tetrakis(triphenylphosphine)palladium (3.5 mg) and potassium carbonate (127 mg) were added, followed by stirring under reflux for 18 hours. To the reaction solution was added 1 N aqueous hydrochloric acid/chloroform, and the resulting organic layer was dried over sodium sulfate, followed by concentration under reduced pressure. The residue was subjected to silica gel column chromatographic purification (developing solvent: chloroform/n-hexane=6/4) to yield Exemplary Compound (1) (34 mg). The compound was identified by $^1$H-NMR.

$^1$H-NMR (CDCl$_3$) δ: 0.90 (6H, t), 0.94-1.41 (22H, m), 1.60-2.04 (10H, m), 2.36 (6H, s), 3.62 (2H, d), 3.83(2H, d), 7.01(2H, d), 7.33(2H, s), 7.64(2H, d), 7.72(1H, d), 7.75(1H, d), 7.91(1H, d), 7.94(1H, d), 13.51(1H, s), 13.52(1H, s)

Synthesis of Compound Example (3)

Compound example (3) was synthesized by the same synthesis method as Compound example (1).

(Synthesis of Exemplary Compound (3))

$^1$H-NMR (CDCl$_3$) δ: 0.87-1.63 (23H, m), 1.78-2.01 (6H, m), 1.37 (6H, s), 2.50-2.61 (1H, m), 7.34 (2H, s), 7.34 (2H, d), 7.62 (2H, d), 7.75 (1H, d), 7.77 (1H, d), 7.92 (1H, d), 7.95 (1H, d), 13.49 (1H, s), 13.50 (1H, s)

Synthesis of Compound Example (17)

Compound example (17) was synthesized in accordance with the following scheme.

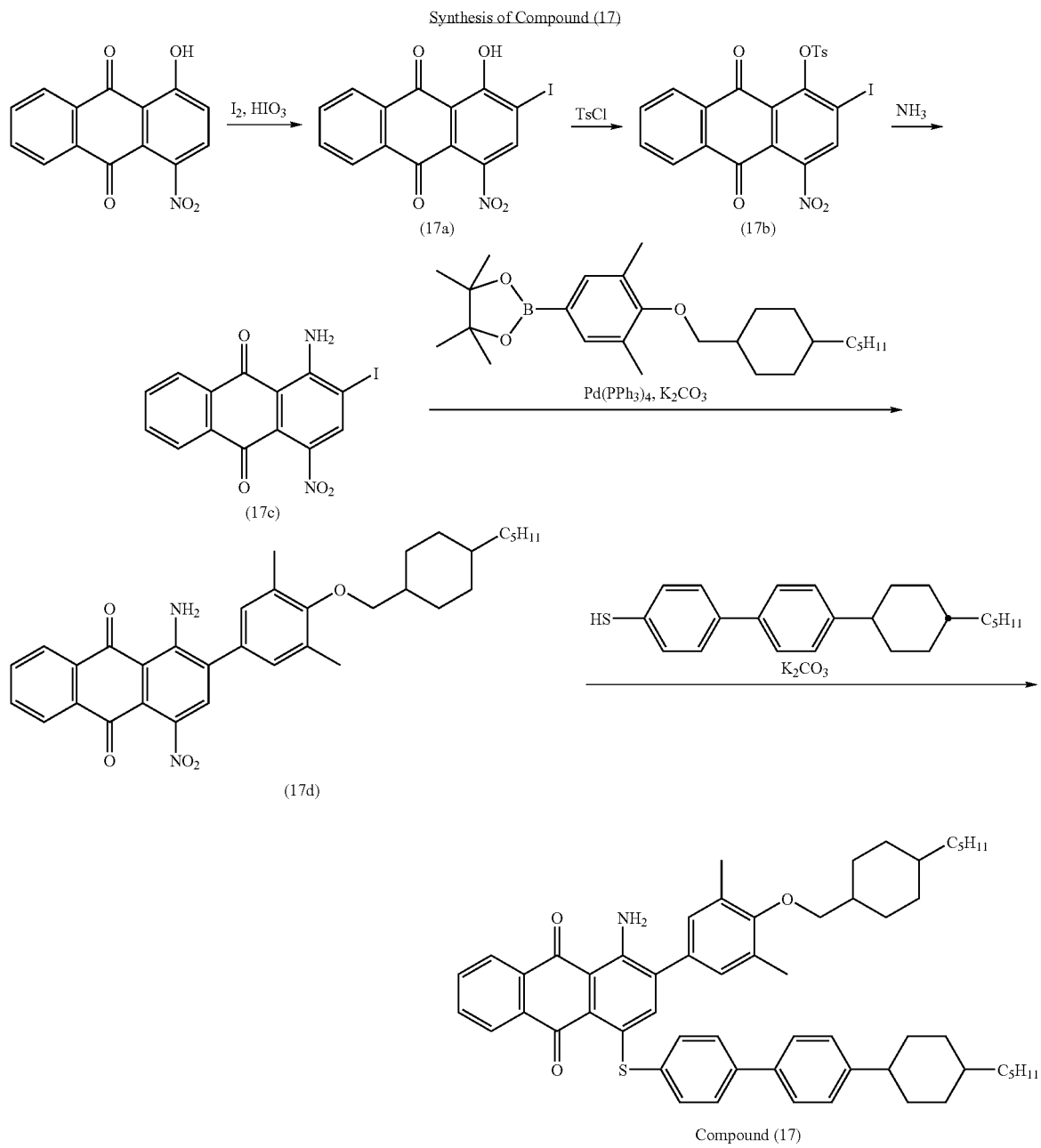

(Synthesis of Compound 17a)

To acetic acid (40 ml), 1-hydroxy-4-nitroanthraquinone (1.0 g), iodine (2.8 g) and iodic acid (1.3 g) were added, and the mixture was heated to 110° C. and stirred for 3 hours. Further, iodine (1.4 g) and iodic acid (0.7 g) were added, followed by stirring at 110° C. for 3 hours. Water was added to the reaction solution, followed by collection of formed crystals by filtration. The crystals were washed with methanol and n-hexane to yield Compound 17a (1.4 g).

(Synthesis of Compound 17b)

Compound 17a (500 mg), tosyl chloride (360 mg), and potassium carbonate (530 mg) were added to dehydrated N-methylpyrrolidone (20 ml), and the mixture was heated to 80° C. After stirring for 2 hours, tosyl chloride (120 mg) was further added, followed by stirring for 1 hour. After cooling at rest, 1N aqueous hydrochloric acid and ethyl acetate were added, and the organic layer was washed with 1N aqueous hydrochloric acid twice, and then was dried over sodium sulfate, followed by concentration under reduced pressure. The residue was dissolved in a small amount of chloroform, and then methanol was added to cause recrystallization. The crystals formed were collected by suction filtration to obtain Compound 17b (430 mg).

(Synthesis of Compound 17c)

Compound 17b (100 mg) was dissolved in dehydrated N-methylpyrrolidone (5 ml), and a 7N-NH$_3$ solution in methanol (1 ml) was added at room temperature. The mixture was heated slowly and was stirred at 60° C. for 1 hour. After cooling at rest, 1N aqueous hydrochloric acid and ethyl acetate were added, and the organic layer was washed with 1N aqueous hydrochloric acid twice, and then was dried over sodium sulfate, followed by concentration under reduced pressure. The residue was subjected to silica gel column chromatographic purification (developing solvent: chloroform) to yield Compound 17c (20 mg).

(Synthesis of Compound 17d)

To a solution of Compound 17c (200 mg) and Compound 1c (250 mg) in toluene (20 ml)/H$_2$O (10 ml), tetrakis(triphenylphosphine)palladium (12 mg) and potassium carbonate (423 mg) were added, followed by stirring under reflux for 18 hours. After cooling at rest, 1 N aqueous hydrochloric acid/chloroform was added thereto and the resulting organic layer was dried over sodium sulfate, followed by concentration under reduced pressure. The residue was dissolved in a small amount of chloroform, and then methanol was added to cause recrystallization. The crystals formed were collected by suction filtration to obtain Compound 17d (90 mg).

(Synthesis of Exemplary Compound (17))

Compound 17d (100 mg), pentylcyclohexylbiphenyltiol (80 mg), and potassium carbonate (70 mg) were added to dehydrated N-methylpyrrolidone (7 ml), and the mixture was heated to 100° C. and stirred for 1 hour. After cooling at rest, 1 N aqueous hydrochloric acid/chloroform was added thereto and the resulting organic layer was dried over sodium sulfate, followed by concentration under reduced pressure. The residue was subjected to silica gel column chromatographic purification (developing solvent: chloroform/n-hexane=7/3) to yield Exemplary Compound (17) (50 mg). The compound was identified by $^1$H-NMR.

$^1$H-NMR (CDCl$_3$) δ: 0.87-2.00 (41H, m), 2.22 (6H, s), 2.48-2.59 (1H, m), 3.56 (2H, d), 6.87 (2H, s), 6.96 (1H, s), 7.30 (2H, d), 7.52 (2H, d), 7.59-7.67 (4H, m), 7.76-7.81 (2H, m), 8.32-8.41 (2H, m)

Synthesis of Compound Example (19)

Compound example (19) was synthesized in accordance with the following scheme.

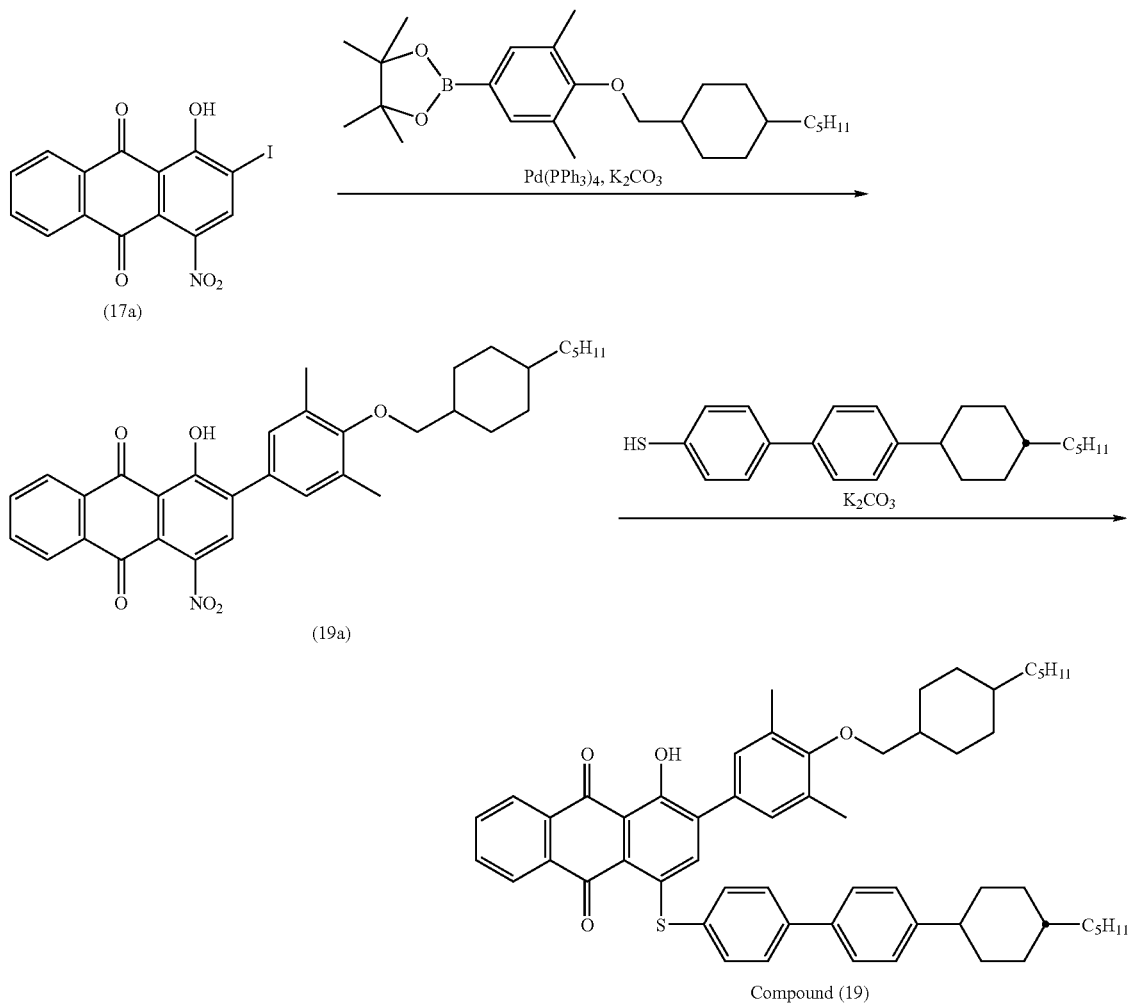

(Synthesis of Compound 19a)

To a solution of Compound 17a (2.0 g) and Compound 1c (2.5 g) in toluene (100 ml)/H$_2$O (50 ml), tetrakis(triphenylphosphine)palladium (117 mg) and potassium carbonate (4.2 g) were added, followed by stirring under reflux for 18 hours. After cooling at rest, 1 N aqueous hydrochloric acid/chloroform was added thereto and the resulting organic layer was dried over sodium sulfate, followed by concentration under reduced pressure. The residue was dissolved in a small amount of chloroform, and then methanol was added to cause recrystallization. The crystals formed were collected by suction filtration to obtain Compound 19a (1.5 g).

(Synthesis of Exemplary Compound (19))

Compound 19a (200 mg), pentylcyclohexylbiphenylthiol (160 mg), and potassium carbonate (150 mg) were added to dehydrated N-methylpyrrolidone (10 ml), and the mixture was heated to 80° C. and stirred for 1 hour. After cooling at rest, 1 N aqueous hydrochloric acid/chloroform was added thereto and the resulting organic layer was dried over sodium sulfate, followed by concentration under reduced pressure. The residue was subjected to silica gel column chromatographic purification (developing solvent: chloroform/n-hexane=7/3) to yield Exemplary Compound (19) (100 mg). The compound was identified by $^1$H-NMR.

$^1$H-NMR (CDCl$_3$) δ: 0.87-1.59 (32H, m), 1.66-2.00 (9H, m), 2.20 (6H, s), 2.48-2.60 (1H, m), 7.07(2H, s), 7.19(1H, s), 7.33 (2H, d), 7.53 (2H, d), 7.78-7.91 (2H, m), 8.37 (1H, dd), 8.43 (1H, dd), 14.08 (1H, s)

<Measurement of Solubility>

Compounds 1, 3, 17 and 19 of the present invention, Comparative Dye A-1 disclosed in Mol. Cryst. Liq. Cryst. Vol. 91, 1983, pages 327 to 340, and Comparative Dye A-2 disclosed in JP-A No. 58-57488 were dissolved separately in a ZLI-2806 liquid crystal (produced by E. Merck) saturatedly. After lapse of a long time, each supernatant liquid portion was injected into a liquid crystal cell (polyimide alignment film, rubbing treatment, parallel alignment, glass plate of 0.7 mm in thickness, cell gap of 8 μm, with an epoxy resin seal, produced by E. H. C.) to prepare evaluation cells. Separately, reference cells were prepared by dissolving each dye at a concentration as low as the dye could be dissolved completely.

To each cell, a polarized light parallel to the rubbing direction and a polarized light perpendicular to that direction were applied, and absorption spectrum (A∥ and A⊥) was measured using an ultraviolet and visible spectrophotometer (UV2400PC) manufactured by Shimadzu Corporation. From the A∥ and A⊥ at the maximum absorption wavelength, a solubility was calculated in accordance with the following Formula 1. The measurement results are shown in Table 1.

Solubility (% by weight)=(Weight concentration of referential liquid crystal composition)·((A∥+A⊥) of evaluation cell)/((A∥+A⊥) of referential cell)   Formula 1

<Measurement of Order Parameter>

Compounds 1, 3, 17 and 19 of the present invention, the aforementioned Comparative Dyes A-1 and A-2 were dissolved separately in ZLI-2806 (trade name, manufactured by E. Merck) to prepare liquid crystal compositions. The contents of the dyes were determined to 0.5% by weight, 0.5% by weight, 1.0% by weight, 1.0% by weight, 0.1% by weight, and 0.5% by weight, respectively, in consideration of the aforementioned solubilities.

Each of the obtained liquid crystal compositions was injected into a liquid crystal cell (polyimide alignment film, rubbing treatment, parallel alignment, glass plate of 0.7 mm in thickness, cell gap of 25 μm, with an epoxy resin seal, produced by E. H. C.) to prepare evaluation cells.

To each of the cells, a polarized light parallel to the rubbing direction and a polarized light perpendicular to that direction were applied, and absorption spectrum (A∥ and A⊥) was measured using an ultraviolet and visible spectrophotometer (UV2400PC) manufactured by Shimadzu Corporation. From the A∥ and A⊥ at the maximum absorption wavelength, an order parameter S was calculated in accordance with the following Formula 2. The measurement results are shown in Table 1.

S=(A∥−A⊥)/(A∥+2·A⊥)   Formula 2

TABLE 1

| Compound | Solubility (% by weight) | Order parameter S | Remarks |
|---|---|---|---|
| 1 | 3 | 0.82 | The present invention |
| 3 | 8 or more | 0.80 | The present invention |
| 17 | 8 or more | 0.80 | The present invention |
| 19 | 8 or more | 0.80 | The present invention |
| A-1 | 0.15 | 0.70 | Comparative example |
| A-2 | 3 | 0.73 | Comparative example |

The order parameters disclosed in the following documents to which reference was made are shown in Table 2.

TABLE 2

| Compound | Order parameter S | Remarks |
|---|---|---|
| A-3 | 0.73 | Comparative example |
| A-4 | 0.77 | Comparative example |
| A-5 | 0.75 | Comparative example |

Comparative Compound

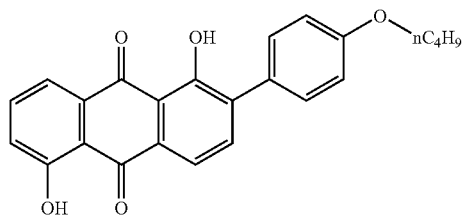

A-1

Disclosed in Mol. Cryst. Liq. Cryst. Vol. 91, 1983, pp. 327 to 340

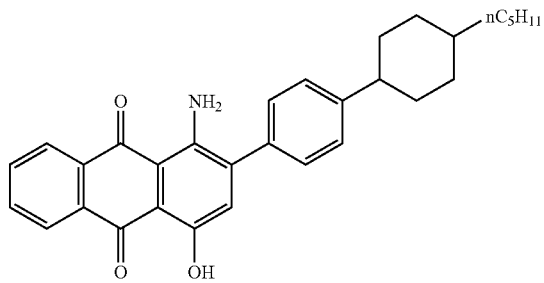

A-2

Disclosed in JP-A No. 58-57488

-continued

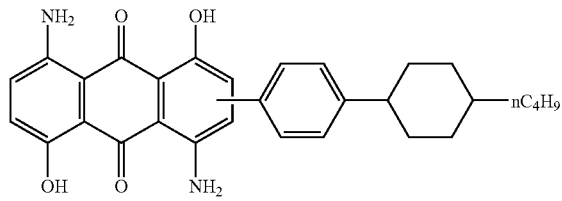
A-3
Disclosed in JP-A No. 58-57488

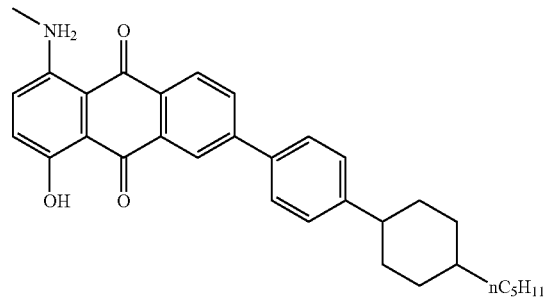
A-4
Disclosed in JP-A No. 57-98561

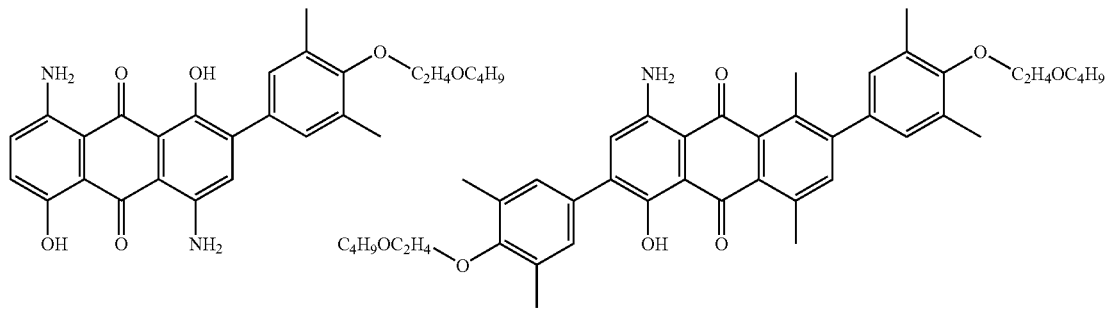
A-5
(6:1)
Disclosed in JP-A No. 58-187454

Table 1 and Table 2 clearly show that the solubility was increased dramatically by Compounds 1, 3, 17 and 19 of the present invention and that they show far higher order parameters than those of Comparative Compounds A-2, A-3 and A-4 each having one liquid crystalline substituent and Comparative Compound A-5 not having a liquid crystalline substance with an improved solubility.

Example 2

<Production of Liquid Crystal Device>

(Preparation of Liquid Crystal Composition)

3.3 mg of the Exemplary Compound (3) as a dichroic dye, 100 mg of ZLI-2806 (trade name, manufactured by E. Merck) as a host liquid crystal, and 0.36 mg of R-1011 (manufactured by E. Merck) as a chiral reagent were mixed and the mixture was heated on a hot plate at 150° C. for one hour. The liquid crystal composition was cooled to room temperature and was left at rest overnight.

(Preparation of Liquid Crystal Device)

The liquid crystal composition was injected into a liquid crystal cell manufactured by Nippo Electric Co., Ltd. (with ITO transparent electrode, and polyimide alignment film SE-1211 (perpendicular alignment) manufactured by Nissan Chemical Industries, Ltd., glass plate of 1.1 mm in thickness, cell gap of 8 μm, with epoxy resin seal) to prepare a liquid crystal device.

(Electric Field Drive)

The obtained liquid crystal device was in a colorless and transparent state when no voltage was applied. The liquid crystal layer was changed to a colored state when a voltage (20 V, 100 Hz) was applied using a signal generator (manufactured by Tektronix, Inc.).

UV/VIS absorption spectra (UV2400 manufactured by Shimadzu Corp.) of the colored state/the colorless and transparent state at the maximum absorption wavelength of a dichroic dye were performed, and the transmittance was measured for the colored state/the colorless and transparent state. The transmittance ratio of the transparent state to the colored state (T (transparent)/T(colored)) was 6. It was confirmed that the liquid crystal devices of the present invention showed high contrast ratios and they can be used suitably for light modulating material or electronic papers.

(Check of Viscosity)

Comparative Dyes A-1, A-2 and Compounds 3, 17 and 19 of the present invention were added separately to a ZLI-2806 liquid crystal (manufactured by E. Merck) and were heated on a hot plate at 150° C. to dissolve so that the concentration might become 8% by weight in each liquid crystal composition. A-1 and A-2 failed to dissolve completely.

After leaving at rest for one day, the sample bottles were tilted. The liquid crystal compositions containing Compounds 3, 17 and 19 exhibited good fluidity. In contrast, the liquid crystal compositions containing A-1 and A-2 did not exhibit fluidity at all.

From the fact shown above, it was confirmed that Compounds 3, 17 and 19 of the present invention are highly compatible with the host liquid crystal and suppresses increase in viscosity due to the addition of the dye.

The foregoing description of the embodiments of the invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

All publications, patent applications, and technical standards mentioned in this specification are herein incorporated by reference to the same extent as if each individual publication, patent application, or technical standard was specifically and individually indicated to be incorporated by reference.

What is claimed is:

1. A liquid crystal composition comprising a compound represented by the following Formula (1) and a liquid crystal:

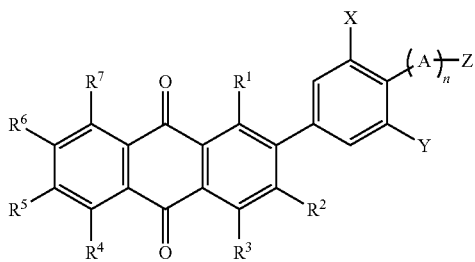

Formula (1)

wherein in Formula (1), at least one of $R^1$, $R^2$, $R^3$, $R^4$, $R^5$, $R^6$ or $R^7$ is a liquid crystalline substituent, and those among $R^1$, $R^2$, $R^3$, $R^4$, $R^5$, $R^6$ and $R^7$ that are not a liquid crystalline substituent each independently represent a hydrogen atom or a substituent; X and Y each independently represent an alkyl group, a halogen atom, an alkoxy group, or an alkylthio group; Z represents an alkyl group having 3 or more carbon atoms, an acyl group, or an aryl group; A represents an oxygen atom, a sulfur atom, or a nitrogen atom; and n represents 0 or 1.

2. The liquid crystal composition according to claim 1, wherein the compound represented by Formula (1) is a compound represented by the following Formula (2):

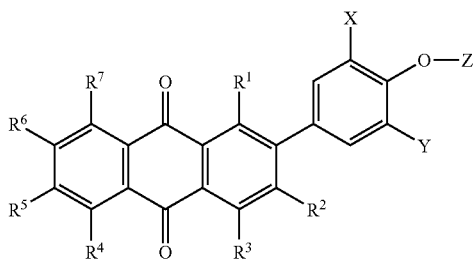

Formula (2)

wherein in Formula (2), at least one of $R^1$, $R^2$, $R^3$, $R^4$, $R^5$, $R^6$ or $R^7$ is a liquid crystalline substituent, and those among $R^1$, $R^2$, $R^3$, $R^4$, $R^5$, $R^6$ and $R^7$ that are not a liquid crystalline substituent each independently represent a hydrogen atom or a substituent; X and Y each independently represent an alkyl group, a halogen atom, an alkoxy group, or an alkylthio group; and Z represents an alkyl group having 3 or more carbon atoms, an acyl group, or an aryl group.

3. The liquid crystal composition according to claim 2, wherein in the compound represented by Formula (2), X and Y are each independently an alkyl group or a chlorine atom.

4. The liquid crystal composition according to claim 2, wherein in the compound represented by Formula (2), Z is an alkyl group having 3 or more carbon atoms.

5. The liquid crystal composition according to claim 1, wherein in the compound represented by Formula (1), Z is an alkyl group represented by the following Structural Formula (A):

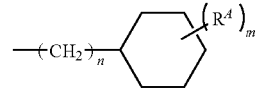

Structural Formula (A)

wherein in Structural Formula (A), n represents an integer of from 0 to 40, m represents an integer of from 0 to 5, and $R^A$ represents a substituent.

6. The liquid crystal composition according to claim 1, wherein in the compound represented by Formula (1), Z is an alkyl group represented by the following Structural Formula (B);

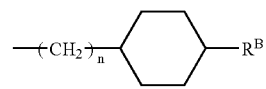

Structural Formula (B)

wherein in Structural Formula (B), n represents an integer of from 0 to 40, and $R^B$ represents an alkyl group having 1 to 30 carbon atoms.

7. The liquid crystal composition according to claim 1, wherein the ratio of the compound represented by Formula (1) to the liquid crystal is from 0.1% by weight to 15% by weight.

8. A liquid crystal device comprising a pair of electrodes at least one of which is a transparent electrode, and a liquid crystal layer disposed between the pair of electrodes which comprises the liquid crystal composition according to claim 1.

9. A reflection display material comprising the liquid crystal device according to claim 8.

10. A light modulating material comprising the liquid crystal device according to claim 8.

11. A compound represented by the following Formula (1):

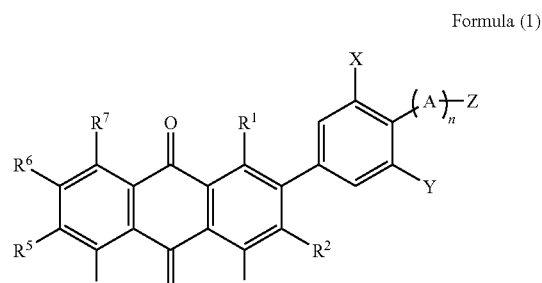

Formula (1)

wherein in Formula (1), at least one of $R^1$, $R^2$, $R^3$, $R^4$, $R^5$, $R^6$ or $R^7$ is a liquid crystalline substituent, and those among $R^1$, $R^2$, $R^3$, $R^4$, $R^5$, $R^6$ and $R^7$ that are not a liquid crystalline substituent each independently represent a hydrogen atom or a substituent; X and Y each independently represent an alkyl group, a halogen atom, an alkoxy group, or an alkylthio group; Z represents an alkyl group having 3 or more carbon atoms, an acyl group, or an aryl group; A represents an oxygen atom, a sulfur atom, or a nitrogen atom; and n represents 0 or 1.

12. The compound according to claim 11, wherein the compound represented by Formula (1) is a compound represented by the following Formula (3):

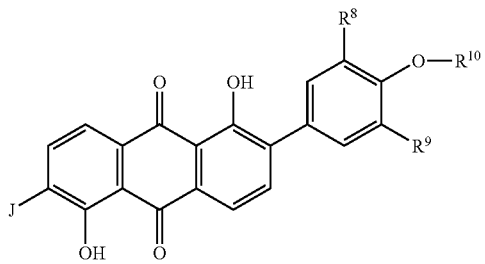

Formula (3)

wherein in Formula (3), $R^8$ and $R^9$ each independently represent an alkyl group; $R^{10}$ represents an alkyl group having 3 or more carbon atoms; and J represents a liquid crystalline substituent.

13. The compound according to claim 11, wherein the compound represented by Formula (1) is a compound represented by the following Formula (4):

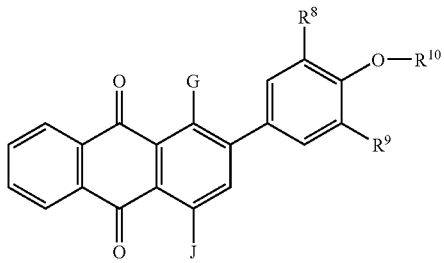

Formula (4)

wherein in Formula (4), $R^8$ and $R^9$ each independently represent an alkyl group; $R^{10}$ represents an alkyl group having 3 or more carbon atoms; J represents a liquid crystalline substituent; and G represents a hydroxyl group or an amino group.

14. The liquid crystal composition according to claim 11, wherein in the compound represented by Formula (1), Z is an alkyl group represented by the following Structural Formula (A):

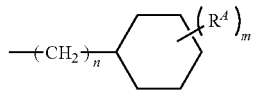

Structural Formula (A)

wherein in Structural Formula (A), n represents an integer of from 0 to 40, m represents an integer of from 0 to 5, and $R^A$ represents a substituent.

15. The liquid crystal composition according to claim 11, wherein in the compound represented by Formula (1), Z is an alkyl group represented by the following Structural Formula (B):

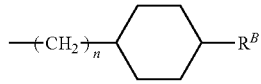

Structural Formula (B)

wherein in Structural Formula (B), n represents an integer of from 0 to 40, and $R^B$ represents an alkyl group having 1 to 30 carbon atoms.

* * * * *